United States Patent [19]
Henry

[11] Patent Number: 6,074,822
[45] Date of Patent: *Jun. 13, 2000

[54] METHOD FOR TESTING FOR RISK OF DIABETES

[75] Inventor: Douglas N. Henry, East Lansing, Mich.

[73] Assignee: Board of Trustees operating Michigan State University, East Lansing, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/740,784

[22] Filed: Nov. 1, 1996

Related U.S. Application Data

[60] Provisional application No. 60/006,210, Nov. 3, 1995.

[51] Int. Cl.[7] .............................. C12Q 1/68; C12P 19/34
[52] U.S. Cl. .............................. 435/6; 435/91.5; 514/866
[58] Field of Search .......................... 435/6, 91.5, 91.51, 435/240.2; 536/24.1, 24.3, 24.31; 935/77, 78; 514/866

[56] References Cited

PUBLICATIONS

Orkin et al. Report and Recommendations of the Panel to Assess the NIH Investment & Research on Gene Therapy pp. 1–38, 1995.
Correll et al. Human Gene Therapy. 1:277–287, 1990.
Paillard. Human Gene Therapy 8:2009–2010, 1997.
James. Antiviral Chemistry & Chemotherapy 2(4):191–214, 1991.
Westermann et al. Biomed. Biochim. Acta 1:85–93, 1989.
Stevens et al. Am J. Physiol. 265(Endocrinol. Metab. 28): E428–E438, 1993.
Henry et al. J Am Soc. Nephrol. 6(3):362, Sep. 1995.
Ruepp et al. Proc. Natl. Acad. Sci. 93:8624–8629, Aug. 1996.
Graham et al. J. Biol. Chem. 266:6872–6877, Apr. 1991.
Stratagene Calatog 1988, p. 39, 1988.
Jones et al, eds RNA Isolation and Analysis BIOS Scientific Publishers pp. 95–109, 128, 133–143, 1994.
Bigler et al. Clin. Res. 37(1):A127, Jan. 1989.
Nishimura et al. Diabetologia 37:328–330, Mar. 1994.
Shah et al. J. Amer. Soc. Nephrol. 5(3):384, Sep. 1994.
Henry et al J. Clin. Invest. 92:617–623, Aug. 1993.
Wang et al. J. Biol. Chem. 268:16052–16058, Jul. 1993.
Ko et al. Diabetes 44:727–732, Jul. 1995.
Tomlinson et al. Trends in Pharmacol. Sci 15:293–297, Aug. 1994.
Hamada et al. Diabetes 40:1233–1240, Oct. 1991.
Sun, Y., et al Variability in the Structure & Expression of the Aldose REductase (AR) Gene Modulates the Risk for Diabetic Nephropathy, JASN vol. 7, No. 9 (1996) (Abstract).
Shah, V.O., et al, Aldose REductase Gene Expression Is Increased in Diabetic Nephropathy, Journal of clinical Endocrinology and Metabolism 82:229402298 (1997).
Patel, A., et al, Chromosome 7q35 and Susceptibility to Diabetic Microvascular Complications, Journal of Diabetes and its Complications 10:62–67 (1996).
Heesom, AE, et al Polymorphism in the 5'–end of the aldose reductase gene is strongly associated with the development of diabetic nephropathy in type I diabetes. Diabetes 46(2):287–291 (1997) (Abstract).
Kicic E, Palmer, Increased white cell aldose reductase mRNA levels in diabetic patients. Diabetic Res. Clin Pract 33(1):31–36 (1996) (Abstract).
Ito, T., et al The level of erythrocyte aldose reductase: a risk factor for diabetic neuropathy? Diabetes Res Clin. Pract. 36(3):161–167) (Abstract).

*Primary Examiner*—Lisa B. Arthur
*Assistant Examiner*—Jehanne Souaya
*Attorney, Agent, or Firm*—Ian C. McLeod

[57] ABSTRACT

A test method and test kit for determining a risk of diabetic complications based upon abnormal aldose reductase genetic material expression is described. Cells isolated from a patient which exhibit elevated levels of aldose reductase genetic material expression at pathophysiologic levels of glucose (about 20 mM) which can occur commonly in the cells of diabetic patients are evaluated based upon a level of expression of DNA or RNA in the cells with the glucose at the pathophysiologic level. The cells can be used to isolate DNA or RNA for a probe which detects the abnormal aldose reductase gene expression. The method can be used to determine when particular aldose reductase inhibitors can be effective for a particular patient.

10 Claims, 10 Drawing Sheets

Basal AR expression in different RPE cell lines.

0 2M 2C 2MC 4M 4C 4MC 8M 8C 8MC

Northern of RPE 45 cell line used in nuclear run-on.

Aldose reductase 5' vimentin pBS

AR cDNA
on Northern

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH:  444
       (B) TYPE:  Nucleic Acid
       (C) STRANDEDNESS:  Single
       (D) TOPOLOGY:  Linear (ii) MOLECULE TYPE: DNA (iii) HYPOTHETICAL: No (iv) ANTI-SENSE: No (v) FRAGMENT TYPE:

(vi) ORIGINAL SOURCE:
       (A) ORGANISM: Human
       (B) STRAIN:  N/A
       (C) INDIVIDUAL ISOLATE:  N/A
       (D) DEVELOPMENTAL STAGE: N/A
       (E) HAPLOTYPE:  N/A
       (F) TISSUE TYPE: N/A
       (G) CELL TYPE: N/A
       (H) CELL LINE: N/A
       (I) ORGANELLE:  N/A (vii) IMMEDIATE SOURCE:  N/A (viii) POSITION IN GENOME:  exons 2-6 of aldose reductase gene
       (10 exons)

(ix) FEATURE:
       (A) NAME/KEY: cDNA
       (B) LOCATION:
       (C) IDENTIFICATION METHOD: sequencing
       (D) OTHER INFORMATION: cDNA encoding aldose reductase (x) PUBLICATION INFORMATION:

(xi) SEQUENCE DESCRIPTION: SEQ ID NO:1:

```
AGAAGCTCAG GGAGCAGGTG GTGAAGCGTG AGGAGCTCTT                40

CATCGTCAGC AAGCTGTGGT GCACGTACCA TGAGAAGGGC                80

CTGGTGAAAG GAGCCTTGCC AGAAGACACT CAGCGACCTG               120

AAGCTGGACT ACCTGGACCT CTACCTTATT CACTGGCCGA               160

CTGGCTTTAA GCCTGGGAAG GAATTTTTCC CATTGGATGA               200

GTCGGGCAAT GTGGTTCCCA GTGACACCAA CATTCTGGAC               240

ACGTGGGCGG CCATGGAAGA GCTGGTGGAT GAAGGGCTGG               280

TGAAAGCTAT TGGCATCTCC AACTTCAACC ATCTCCAGGT               320

GGAGATGATC TTAAACAAAC CTGGCTTGAA GTATAAGCCT               360

GCAGTTAACC AGATTGAGTG CCACCCATAT CTCACTCAGG               400

AGAAGTTAAT CCAGTACTGC CAGTCCAAAG GCATCGTGGT               440

GACC                                                     444
```

(2) INFORMATION FOR SEQ ID NO:2:

(i) SEQUENCE CHARACTERISTICS:
       (A) LENGTH:  463

```
      (B) TYPE: Nucleic acid
      (C) STRANDEDNESS: Single
      (D) TOPOLOGY: Linear (ii) MOLECULE TYPE: DNA (iii) HYPOTHETICAL: No (iv) ANTI-SENSE: No (v) FRAGMENT TYPE:

(vi) ORIGINAL SOURCE:
      (A) ORGANISM: Human
      (B) STRAIN: N/A
      (C) INDIVIDUAL ISOLATE: N/A
      (D) DEVELOPMENTAL STAGE: N/A
      (E) HAPLOTYPE: N/A
      (F) TISSUE TYPE: N/A
      (G) CELL TYPE: N/A
      (H) CELL LINE: N/A
      (I) ORGANELLE: N/A (vii) IMMEDIATE SOURCE: N/A (viii) POSITION IN GENOME: exons 2 to 6 of aldose
       reductase gene (10 exons)

(ix) FEATURE:
      (A) NAME/KEY: cDNA
      (B) LOCATION:
      (C) IDENTIFICATION METHOD: sequencing
      (D) OTHER INFORMATION: DNA encoding
          aldehyde reductase (x) PUBLICATION INFORMATION:

(xi) SEQUENCE DESCRIPTION: SEQ ID NO:2:

TGCTACGACT CCACCCACTA CAAGGAGACT TGGAAGGCTC              40

TGGAGGCACT GGTGGCTAAG GGGCTGGTGC AGGCGCTGGG             80

CCTGTCCAAC TTCAACAGTC GGCAGATTGA TGACTTACTC            120

AGTGTGGCCT CCGTGCGTCC AGCTGTCTTG CAGGTGGAAT            160

GCCACCCATA CTGGGCTCAA AATGAGCTAA TTGCCCACTG            200

CCAAGCACGT GGCTTGGAGG TAACTGCTTA TAGCCCTTTG            240

GGCTCCTCTG ATCGTGCATG GCGTGATCCT GATGAGCCTG            280

TCCTGCTGGA GGAACCAGTA GTCCTGGCAT TGCTGAAAAG            320

TATGGCCGAT CTCCAGCTCA GATCTTGCTC AGGTGGCAGG            360

TCCAGCGGAA AGTGATCTGC ATCCCCAAAA GTATCACTCC            400

TTCTCGAATC CTTCAGAACA TCAAGGTGTT TTACTTCACC            440

TTTAGCCCAG AAGAGATGAA GCA                              463

(2) INFORMATION FOR SEQ ID NO:3:

(i) SEQUENCE CHARACTERISTICS:
      (A) LENGTH: 28
      (B) TYPE: Nucleic Acid
      (C) STRANDEDNESS: Single
      (D) TOPOLOGY: Linear (ii) MOLECULE TYPE: DNA (iii) HYPOTHETICAL: No (iv) ANTI-SENSE: No (v) FRAGMENT TYPE:
```

```
       (vi) ORIGINAL SOURCE:
             (A) ORGANISM: N/A
             (B) STRAIN:  N/A
             (C) INDIVIDUAL ISOLATE:  N/A
             (D) DEVELOPMENTAL STAGE: N/A
             (E) HAPLOTYPE:  N/A
             (F) TISSUE TYPE: N/A
             (G) CELL TYPE: N/A
             (H) CELL LINE: N/A
             (I) ORGANELLE:  N/A (vii) IMMEDIATE SOURCE:  N/A (viii) POSITION IN GENOME:  N/A (ix) FEATURE:
             (A) NAME/KEY: N/A
             (B) LOCATION:
             (C) IDENTIFICATION METHOD: N/A
             (D) OTHER INFORMATION: N/A (x) PUBLICATION INFORMATION:

(xi) SEQUENCE DESCRIPTION: SEQ ID NO:3:

TATAAGCTTG CTACGACTCC ACCCACTA                                          28

(2) INFORMATION FOR SEQ ID NO:4:

(i) SEQUENCE CHARACTERISTICS:
             (A) LENGTH:  29
             (B) TYPE:  Nucleic Acid
             (C) STRANDEDNESS:  Single
             (D) TOPOLOGY:  Linear (ii) MOLECULE TYPE: DNA (iii) HYPOTHETICAL: No (iv) ANTI-SENSE: No (v) FRAGMENT TYPE:

(vi) ORIGINAL SOURCE:
             (A) ORGANISM: N/A
             (B) STRAIN:  N/A
             (C) INDIVIDUAL ISOLATE:  N/A
             (D) DEVELOPMENTAL STAGE: N/A
             (E) HAPLOTYPE:  N/A
             (F) TISSUE TYPE: N/A
             (G) CELL TYPE: N/A
             (H) CELL LINE: N/A
             (I) ORGANELLE:  N/A (vii) IMMEDIATE SOURCE:  N/A (viii) POSITION IN GENOME:  N/A (ix) FEATURE:
             (A) NAME/KEY: N/A
             (B) LOCATION:
             (C) IDENTIFICATION METHOD: N/A
             (D) OTHER INFORMATION: N/A (x) PUBLICATION INFORMATION:

(xi) SEQUENCE DESCRIPTION: SEQ ID NO:4:

ATATCTAGAT GCTTCATCTC TTCTGGGCT                                         29

(2) INFORMATION FOR SEQ ID NO:5:

(i) SEQUENCE CHARACTERISTICS:
             (A) LENGTH:  28
             (B) TYPE:  Nucleic Acid
             (C) STRANDEDNESS:  Single
```

```
         (D) TOPOLOGY:  Linear (ii) MOLECULE TYPE: DNA (iii) HYPOTHETICAL: No (iv) ANTI-SENSE: No (v) FRAGMENT TYPE:

(vi) ORIGINAL SOURCE:
         (A) ORGANISM: N/A
         (B) STRAIN:  N/A
         (C) INDIVIDUAL ISOLATE:  N/A
         (D) DEVELOPMENTAL STAGE: N/A
         (E) HAPLOTYPE:  N/A
         (F) TISSUE TYPE: N/A
         (G) CELL TYPE: N/A
         (H) CELL LINE: N/A
         (I) ORGANELLE:  N/A (vii) IMMEDIATE SOURCE:  N/A (viii) POSITION IN GENOME:  N/A (ix) FEATURE:
         (A) NAME/KEY: N/A
         (B) LOCATION:
         (C) IDENTIFICATION METHOD: N/A
         (D) OTHER INFORMATION: N/A (x) PUBLICATION INFORMATION:

(xi) SEQUENCE DESCRIPTION: SEQ ID NO:5:

TATAAGCTTA GAAGCTCAGG GAGCAGGT                                            28

(2) INFORMATION FOR SEQ ID NO:6:

(i) SEQUENCE CHARACTERISTICS:
         (A) LENGTH:  28
         (B) TYPE:  Nucleic Acid
         (C) STRANDEDNESS:  Single
         (D) TOPOLOGY:  Linear (ii) MOLECULE TYPE: DNA (iii) HYPOTHETICAL: No (iv) ANTI-SENSE: No (v) FRAGMENT TYPE:

(vi) ORIGINAL SOURCE:
         (A) ORGANISM: N/A
         (B) STRAIN:  N/A
         (C) INDIVIDUAL ISOLATE:  N/A
         (D) DEVELOPMENTAL STAGE: N/A
         (E) HAPLOTYPE:  N/A
         (F) TISSUE TYPE: N/A
         (G) CELL TYPE: N/A
         (H) CELL LINE: N/A
         (I) ORGANELLE:  N/A (vii) IMMEDIATE SOURCE:  N/A (viii) POSITION IN GENOME:  N/A (ix) FEATURE:
         (A) NAME/KEY: N/A
         (B) LOCATION:
         (C) IDENTIFICATION METHOD: N/A
         (D) OTHER INFORMATION: N/A
```

-continued (x) PUBLICATION INFORMATION:

(xi) SEQUENCE DESCRIPTION: SEQ ID NO:6:

ATATCTAGAG GTCACCACGA TGCCTTTG                                    28

METHOD FOR TESTING FOR RISK OF DIABETES

CROSS-REFERENCE TO RELATED APPLICATION

This application claims the benefit of U.S. Provisional Application No. 60/006,210, filed Nov. 3, 1995, now abandoned.

GOVERNMENT RIGHTS

This invention was funded by NICHD 1992–1995 Center Grant 1 P30 HD 28820; and NIDDK-NIH Physician Scientist Award 1K11DK02193-01. The U.S. Government has certain rights in this invention.

BACKGROUND OF THE INVENTION (1) Summary of the Invention

The present invention relates to a method for testing for the risk of long-term complications of diabetes based upon expression of genetic material encoding aldose reductase in cells. In particular the present invention relates to an in vitro method which tests the cells in the presence of pathophysiologic levels of glucose for the test. Further, the present invention provides an in vitro method for determining whether a particular aldose reductase inhibitor may be effective against diabetes in a particular patient. Further still, the present invention provides a method for inhibiting aldose reductase expressing genetic material using a vector by delivering DNA or RNA which binds the genetic material in the cells to prevent the expression of aldose reductase.

(2) Description of Related Art

The prior art has recognized that there is a need for an effective method for testing patients for risk of diabetic complications at a cellular level. In general, there has been no method which is available.

There has been extensive research with aldose reductase which is involved in the complications of diabetes; however, no test has been developed for predicting the long-term complications of diabetes. The exact mechanism by which the enzyme is activated to abnormal levels has not been determined.

The success of a Diabetes Control and Complications Trial (DCCT) in 1993 rested in the convincing demonstration that sustained elevated levels of blood glucose increased the risk for the development of long-term complications of diabetes (N Eng J Med. 329:977–986 (1993)). Unanswered by the DCCT was the question why some individuals with elevated blood glucose levels were resistant to the development of these complications while others had excellent blood glucose control but a rapid clinical course to retinopathy, neuropathy or nephropathy. Pathways of glucose metabolism whose flux varies as a function of prevailing hyperglycemia are generally invoked as putative mediators of those chronic diabetic complications whose incidence and/or prevalence most closely parallels the duration and severity of antecedent hyperglycemia. But metabolic pathways, such as the polyol pathway, are rarely invoked to explain the wide variation of diabetic complications among patients with similar degrees of chronic hyperglycemia.

The polyol hypothesis asserts that diabetic complications result, in part, from the direct or indirect consequences of sorbitol production from excess glucose by aldose reductase (AR). Aldose reductase has been thought to be implicated in the development of long-term complications of diabetes for more than a quarter century, yet little is known about the pathogenetic determinants of AR expression in the normal population, subjects with diabetes and the presence or absence of long-term complications of the disease. Recent evidence has linked increased tissue-specific catalytic capacity or protein content AR enzymes with the prevalence and/or severity of diabetic complications, but it is not clear whether this is a cause or an effect. In multiple clinical trials, AR inhibitors (ARIs) have had mixed success (or failure) in the treatment or prevention of long-term complications of diabetes. Nonetheless, part of this limited success with the use of ARIs may be due to the inability to prospectively identify those subjects who would benefit from their use prior to the establishment of irreversible end-organ damage from diabetes.

Heterogeneity of AR protein expression has been hypothesized for almost 12 years beginning with Srivastava's and Das's report of AR activation in human tissues (Srivastava, S. K., et al., Biochim Biophys Acta 800:220–227 (1984)). For more than ten years, a theory of heterogeneity of AR protein activity causing increased susceptibility to long-term complications of diabetes has been proposed (Srivastava, S. K., et al., Biochim Biophys Acta 870:302–311 (1986)). Studies have demonstrated that elevations of ambient glucose will increase AR activity in erythrocytes from both normal and diabetic subjects (Lyons, P. A., et al., Medical Research and Clinical Practice 14:9–14 (1991); Hamada, Y., et al., Diabetes 40:1233–1240 (1991); Ana, H. P., Central African Journal of Medicine 41(6):199–202 (1995); and Funasako, M., et al., Mechanisms of Aging and Development 73:137–143 (1994)) and increased AR protein activity has been associated with the presence or absence of diabetic complications in multiple studies using both erythrocytes or neutrophiles (Hamada, Y., et al., Diabetic Medicine 10:33–38 (1993); Aida, K., et al., Diabetes Care 13(5):461–467 (1990); Nishimura, C., et al., Diabetologia 37:328–330 (1994); and Dent, M. T., et al., Diabetic Medicine 8:439–442 (1991)).

The human AR gene has been identified (Graham, A., et al., J. Bio. Chem. 266(11):6872–6877 (1991)) and mapped to a single locus on the 7q35 human chromosome (Graham, A., et al., Hum Genet 86:509–514 (1991)). While a true polymorphism of the AR gene has never been reported, a restriction length polymorphism to an $(A-C)_n$ dinucleotide repeat (microsatellite DNA 5' of the promoter) has been identified from a population of Chinese subjects with Type II diabetes and found to be associated with the presence of early-onset retinopathy but not nephropathy (Ben, D., et al., Diabetes 44:727–732 (1995)). One study has proposed the existence of a polymorphic site at the first intron (in the noncoding region of the AR gene) which was also associated with retinopathy but not nephropathy (Patell, A., et al., Enzymology and Molecular Biology of Carbonyl Metabolism 4. H. Weine, Ed. Plenum Press, N.Y. pp. 325–332 (1993)). These studies did not determine the levels of AR activity in the populations studied, hence it is not known if expression of an AR "polymorphism" was associated with changes in AR activity or sorbitol production. These human studies have not prospectively identified those subjects who developed complications. Increased steady state levels of AR mRNA have been associated with the presence of diabetic nephropathy but not with non-diabetic causes of nephropathy (Shah, V., et al., ASN 6(3):455 (1995)). Shah, et al. determined that AR/β-actin mRNA ratios were more than 3 fold elevated in those subjects with Type I diabetes and diabetic nephropathy as compared with subjects with diabetes and absence of nephropathy. This study did not determine the levels of AR activity in the study populations.

The use of mRNA to ascertain heterogeneity of gene expression for AR is necessitated by lack of understanding of the genetic determinants of AR expression. Until the regulatory regions of the aldose reductase gene are characterized, analysis of mRNA seems an appropriate system to measure differences in AR gene expression. Nonetheless, these findings do suggest that heterogeneity of AR gene expression exists, and that elevated expression of AR mRNA may be seen in those subjects with diabetic kidney disease (Vinores, S. A., et al., Diabetes 37:1658–1664 (1988)). It is not known if heterogeneity of AR gene expression is genetically determined or an "epi-genetic" phenomena, resulting from the effects of diabetes on AR expression.

Heterogeneity of AR gene expression in primary cultures of human retinal pigment epithelial cells (RPE) has been described (Henry, D. N., et al., J. Clin. Invest. 92(2):617–23 (1993); Stevens, J. M., et al., Am. J. Physiol. 265(3 pt 1):E428–38 (1993); and Henry, D. N., et al., J. Am. Soc. Neph 6(3):362 (1995)). The retinal pigment epithelium supports and nourishes the neuroretinal cells in vivo. RPE cells exhibit glucose-induced, ARI-sensitive physiological impairment manifested by deterioration of electroretinograms in vivo and decreased rod outer segment phagocytosis in vitro, that is prevented by aldose reductase inhibitors (ARIs) (Del Monte, M. A., et al., Diabetes 40:1335–1345 (1991)). Immunohistochemical data suggest that AR protein is more abundant in RPE cells of patients with background or proliferative retinopathy (Vinores, S. A., et al., Diabetes 37:1658–1664 (1988)). Heterogeneity of AR expression in RPE cell cultures parallels AR activity and sorbitol production, and is responsive to the use of aldose reductase inhibitors in vitro. Thus RPE cells constitute a pathophysiologically relevant model in which to assess the effects of AR gene expression and polyol metabolism (Del Monte, M. A., et al., Diabetes 40:1335–1345 (1991)).

Trevisan, et al., (Trevisan, R., et al., Diabetes 41:1239–46 (1992)) have reported that in subjects with IDDM and nephropathy, both peripheral blood erythrocytes and cultured skin fibroblasts demonstrate a greater amiloride-sensitive sodium influx (Na+/H antiport activity) and enhanced cell proliferation than they do in subjects with IDDM and without nephropathy. To determine whether the tendency for NIDDM to run in families could relate to genetically determined defects in insulin stimulation of glycogen synthesis, Wells, et al., cultured forearm skin fibroblasts from subjects with a strong family history of NIDDM and from subjects without any family history of NIDDM as control subjects. Rates of glycogen synthesis were lower in NIDDM subjects both with basal and maximal insulin stimulation (Wells, A. M., et al., Diabetes 41:583–589 (1993)). Okuda, et al. have reported the restoration of myo-inositol uptake by eicosapentaenoic acid in skin fibroblasts cultured in a high glucose medium, and that myo-inositol uptake into skin fibroblasts was dependent on an active Na/K ATPase activity (Okuda, Y., et al., Life Sciences (57)5:71–74 (1995)). Thus, the use of fibroblasts can be used to characterize the pathogenetic expression of AR and diabetes.

An osmotically induced enhancer of aldose reductase gene transcription was identified in the 5'-untranslated region of the gene. This fragment works with both the homologous and a heterologous (thymidine kinase) promoter and was capable of increasing AR gene transcription independent of position and orientation to the promoter (Shiro Maeda, Masaki Togawa, Douglas N. Henry, Douglas A. Greene, Paul D. Killen. Characterization of an Osmotically Activated Enhancer of Aldose Reductase Gene Transcription. J. Am. Society of Nephr. 5(3):3414 (1994)).

The molecular mechanism underlying increased AR mRNA, protein and activity in patients with diabetes remains enigmatic. Otherwise silent genetic mutations which lead to high constitutive AR gene expression or inducibility of AR by elevated ambient glucose may predispose these subjects to perturbations of cellular metabolism linked to the polyol pathway and explain (in part) the clinical heterogeneity of diabetic complications. The early, prospective identification of particular patients prone to diabetic complications would motivate and justify intensive prophylactic metabolic intervention by either intensified metabolic control and/or selected use of aldose reductase inhibitors. Aberrant constitutive, generalized, or tissue-specific overexpression of AR in some patients with diabetes mellitus, whether on a genetic or acquired basis, could constitute such a predisposing factor.

OBJECTS

It is an object of the present invention to provide an in vitro method for testing for a risk of diabetic complications in a human patient.

It is further an object of the present invention to provide an in vitro method which can use an aldose reductase inhibitor to treat the patient.

Further still, it is an object of the present invention to provide a method which uses exogenous DNA or an RNA encoding aldose reductase to bind endogenous DNA in a cell so as to prevent the endogenous DNA or RNA from being expressed.

It is an object of the present invention to provide a method for determining and comparing AR expression (mRNA, protein activity and sorbitol production) from subjects with diabetes (NIDDM) and non-diabetic subjects stratified by age and gender.

Further, it is an object of the present invention to provide a method for determining and comparing AR expression from subjects who have NIDDM with and without diabetic retinopathy and stratified by duration of diabetes, use of insulin, or glycemic control.

Further, it is an object of the present invention to provide a method for determining AR encoding genetic material expression when regulated by pathophysiological levels of glucose in cultured cells from both non-diabetic subjects and subjects with diabetes.

Further, it is an object of the present invention to provide a method for comparing AR encoding genetic material in different cells from the same patient.

Finally, an object of this invention is to provide a method for determining risk factors that lead to retinopathy and progression of retinopathy.

These and other objects of the present invention will become increasingly apparent by reference to the following description and the drawings.

Translation is inhibited by osmotic stress as $^3$H-proline incorporation into trichloroacetic acid (TCA) precipitated proteins is inhibited by 87% in RPE cells exposed to hyperosmolar mannitol which was not due to decreased uptake by hyperosmolar media (data not shown). These data suggest that increases in AR transcription are dependent upon prior protein synthesis but that maintenance of basal level AR transcription is independent of protein synthesis. The duality of transcription regulation may initially permit the cell to increase steady state AR mRNA levels (and ultimately sorbitol as an organic osmolyte) until selective AR transcription and translation can occur during the early events of osmotic challenge.

Figure 8A:
Figure 8B:

FIGS. 8A and 8B are computer scans showing proteins which are selectively translated during these early events using 2-dimensional gel electrophoresis of proteins isolated from RPE cells exposed to isomolar (5 mM) glucose left) hyperosmolar stress with silver staining (300 mM glucose right) after 6 hours. The initial attempt at resolving proteins on 2-D gels were presented as a poster at the Department of Pediatrics 4th Annual Research Symposium on Sep. 23, 1994. "Attenuated Translation in Human Retinal Pigment Epithelial Cells in Response to Hypertonic Stresses In Vitro". Mark Brannon, Philip Andrews, and Douglas Henry).

Figure 9:
Figure 9:
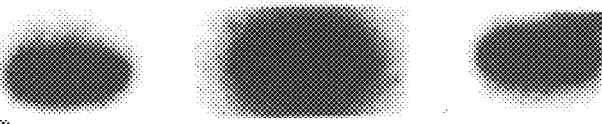
Figure 9:

FIG. 9 is a photograph showing a blot nuclear run-on quantitation of AR transcription from high basal AR expressing RPE isolate (RPE-HE) and low basal AR expressing RPE isolate (RPE-LE) normalized to the levels of vimentin transcription in vitro (upper panel). Northern analysis of steady state AR mRNA from the same isolates used for nuclear run-on studies (lower panel). Differences in steady-state AR-mRNA in these isolates are not due to different rates of AR gene transcription but are probably due to different AR mRNA stabilities. Differences in AR mRNA stability may be responsible for higher basal AR expression in some RPE isolates. Frozen and stored fibroblast from the study subjects of this proposal are a resource for DNA analysis and nuclear run-on studies when the determinants of AR gene regulation are reported (Henry, R. S., et al., Heterogeneity of Aldose Reductase (AR) Gene Expression: Increased Steady State Abundance of AR mRNA Is Not Due to Differences in Basal Transcription. 28th Annual Meeting and Exposition of the American Society of Nephrology, Nov. 5–8 (1995)).

Figure 10:
Figure 10:
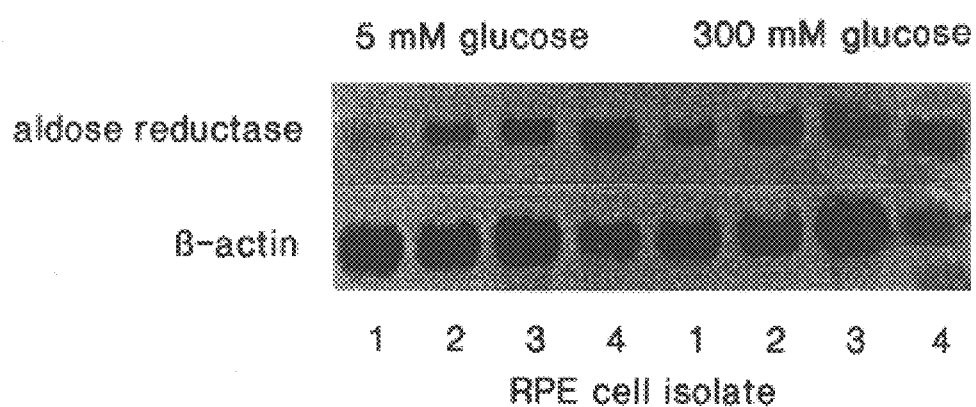

FIG. 10 is a computer scan showing a blot in a test for steady state levels of AR mRNA by Northern analysis from four different primary cultures of human RPE cell isolates in vitro. Cells were grown in normal (5 mM) and hyperosmolar levels of glucose (300 mM) containing media. Hyperosmolar stress is a known inducer of AR but rarely sustained in diabetes. These data demonstrate three different phenotypes of RPE cells; 1) low basal AR expressors, 2) & 3) intermediate AR expressors, and 4) high constitutive AR expressors. These phenotypes are believed to exist in vivo and would show increased susceptibility to AR related development of long-term complications from diabetes (Henry, R. S., et al., 28 Annual Meeting and Exposition of the American Society of Nephrology (Nov. 5–8 (1995)).

Figure 1:
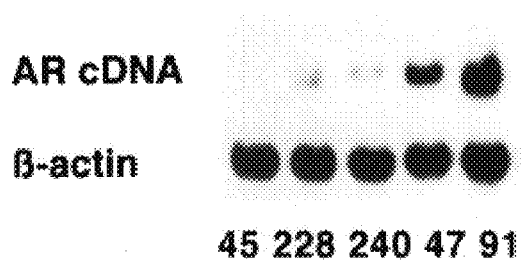
FIG. 1 is a photograph showing heterogeneity of AR expression in four different RPE cell lines. Autoradiogram of RPE total RNA after hybridization with AR cDNA. All cells grown in iso-osmolar glucose (5 mM glucose) media.
Figure 11:
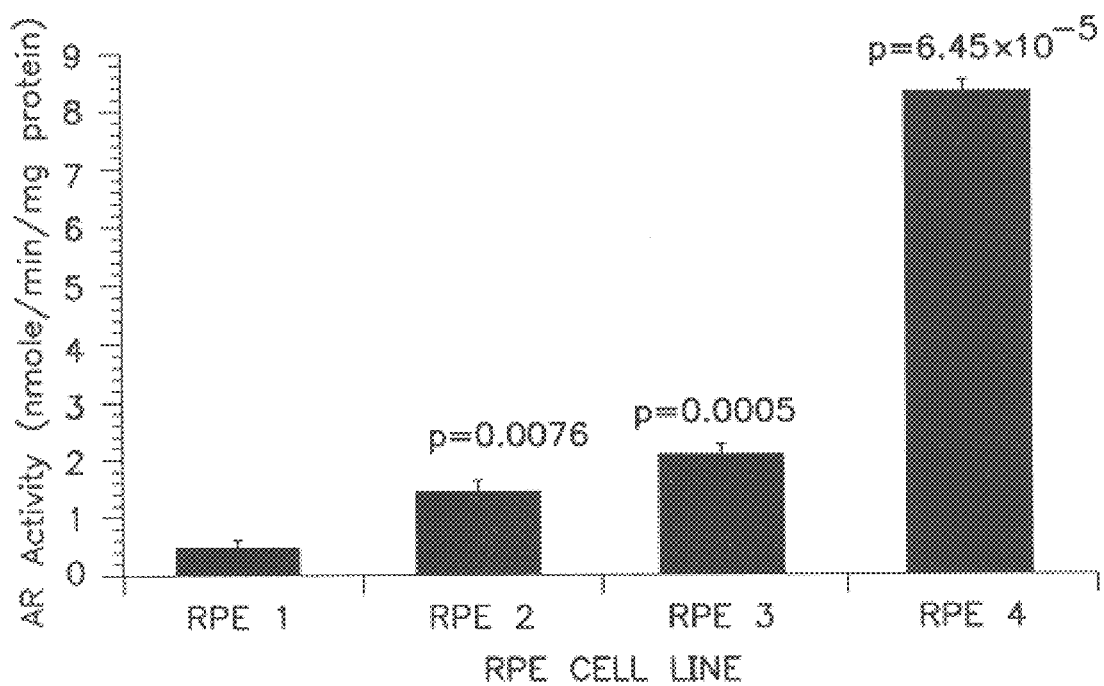

FIG. 11 shows basal AR protein activity in four different human primary RPE isolates from FIG. 1 grown in normal glucose (5 mM) containing media. AR activity is proportional to the basal levels of AR mRNA expression. Increased expression of the gene (FIG. 10) resulted in higher activity of the protein (FIG. 11). Heterogeneity of AR expression in this model has physiological significance as sorbitol levels parallel AR mRNA and protein activity (Henry, R. S., et al., 28 Annual Meeting and Exposition of the American Society of Nephrology (Nov. 5–8 (1995)).

Figure 12:
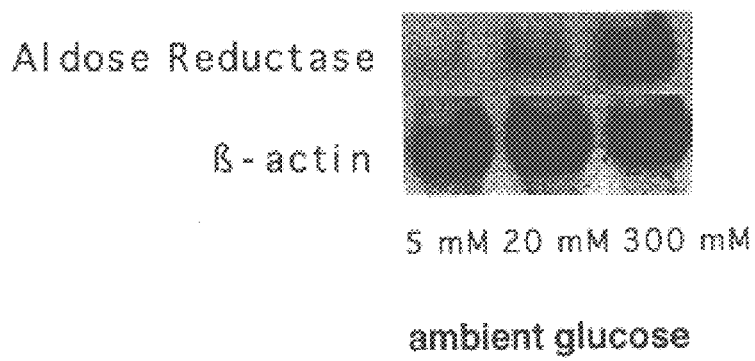

FIG. 12 is a computer scan showing a Northern blot showing induction of AR by pathophysiological level of glucose (20 mM) and hyperosmolar level of glucose (300 mM) in a primary human RPE isolate in vitro. AR activity increased proportionally to the levels of AR mRNA in this isolate (not shown). This is the fourth phenotype of AR expressor from human primary cultures of RPE cells. If this phenotype exists in vivo, heterogeneity of AR expression may be an "epigenetic" phenomena with the presence of diabetes being a primary determinant of altered AR expression.

Figure 13:
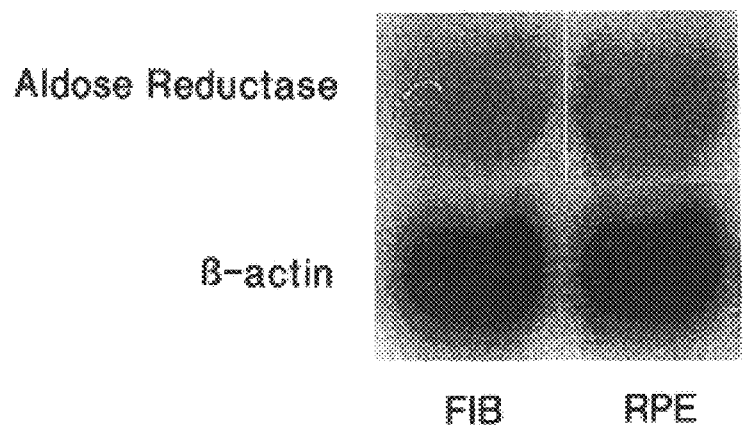

FIG. 13 is a computer scan showing a Northern blot demonstrating similar basal levels of AR mRNA expression from primary fetal cultures of human RPE cells and scleral fibroblast in vitro. Similar levels of AR expression from these different tissues suggest "peripheral" fibroblast accurately reflect the amount of AR expression in the RPE cell layer.

Figure 14:
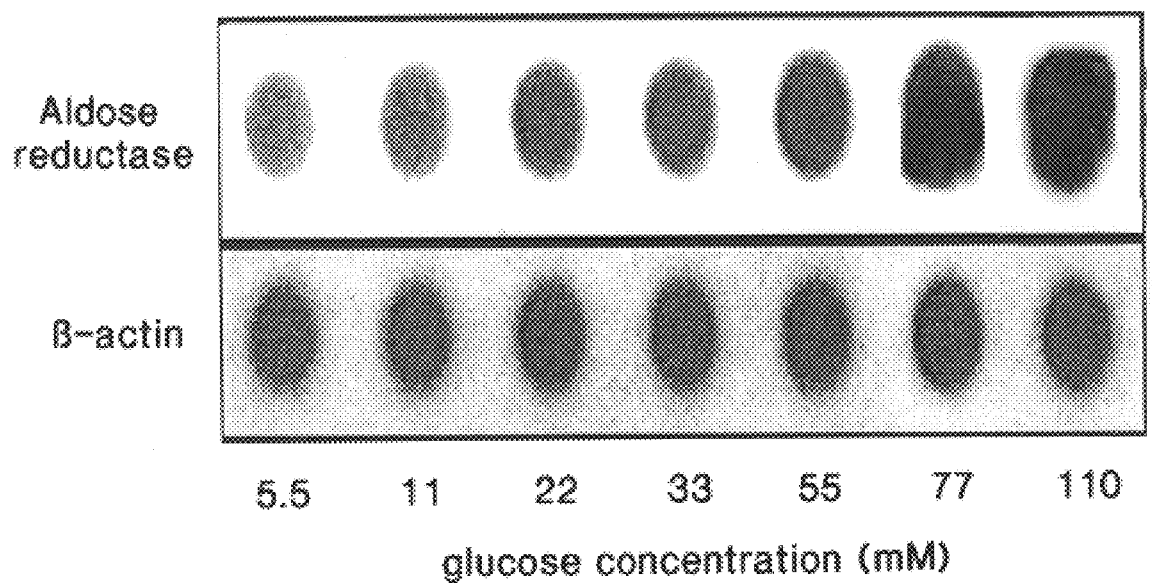

FIG. 14 is a computer scan showing a Northern blot showing dot blot quantitation of induction of AR by increasing concentrations of glucose in human pancreatic ductal cells (CAPAN-1) in vitro. Cells were grown for 48 hours in media containing increasing concentrations of glucose. Induction of AR is seen as early as 11 mM glucose. Dot blots can easily be quantified by scanning densitometry and normalized for loading once blot is stripped of AR cDNA probe and reprobed with β-actin to control for differences in RNA loading (Busik, J. V., et al., Increased Expression of Aldose Reductase mRNA and Enzyme Activity Induced by Pathophysiological and Hyperosmolar Levels of Glucose in CAPAN-1 Pancreatic Duct Cells. Accepted to the American Pancreatic Assoc. Chicago, Ill. Nov. 7–8 (1996)). These data further support the possibility of induction of AR by pathophysiological levels of glucose.

DESCRIPTION OF PREFERRED EMBODIMENTS

The present invention relates to a method of testing cells to determine a risk of diabetic complications in a human patient which comprises:

(a) isolating cells from the patient which can be indicative of the risk of diabetic complications;

(b) exposing the cells from the patient to glucose at pathophysiologic levels which can occur commonly in diabetes; and (c) determining a level of aldose reductase genetic material selected from the group consisting of DNA and RNA encoding reductase and regulatory elements of the genetic material in the cells, wherein an elevated level of aldose reductase gene expression of the genetic material is indicative of a risk of diabetic complications.

The present invention relates to a test kit for determining abnormal aldose reductase genetic material as indicative of a risk of diabetes in a patient which comprises:

(a) a probe of a genetic material selected from the group consisting of exogenous DNA and RNA encoding the reductase and regulating elements of the genetic material provided in a container which exogenous DNA or RNA selectively binds to the endogenous DNA or RNA in cells of the patient;

(b) instructions for use of the probe to bind the endogenous RNA or DNA.

The present invention further relates to a method for the treatment of diabetic complications of a human patient which comprises:

(a) isolating cells from the patient which can be indicative of the risk of diabetic complications;

(b) exposing the cells isolated from the patient to glucose at pathophysiologic levels which can occur commonly in diabetes;

(c) determining in vitro a level of expression of aldose reductase genetic material selected from the group consisting of DNA and RNA encoding the reductase and regulatory elements of the genetic material in the cells, wherein an elevated level of aldose reductase gene expression of the genetic material is indicative of the risk of diabetes complications; and (d) treating the patient with an elevated level of aldose reductase gene expression with an aldose reductase inhibitor.

The cells are taken from a living patient. They include mesodermal cells. Cells can be blood, skin, nerve, renal or eye. The eye cells would be used only in rare circumstances where there is an operation. The skin is the most readily biopsied and is preferred.

known aldose reductase inhibitors are: TOIRESTAT™ AND SORBINIL™ (Phizer, Inc., Norwalk, Conn. These can be used in the method of the present invention.

The test method and kit uses a DNA probe which is selective for DNA or RNA encoding abnormally stable aldose reductase. The nucleotides for RPE cDNA are set forth in SEQ ID NO:1.

The use of fibroblasts has several potential advantages over the use of peripheral blood cells to measure AR mRNA, protein, and activity: 1) erythrocytes or neutrophils are disrupted by diabetic complications (nephropathy/uremia) that may potentially arise from altered aldose reductase. Also, since the genetic determinants of AR gene regulation have yet to be identified, the reactivity of peripheral blood leukocytes to cytokines or intercurrent infection may not accurately reflect the in vivo activation of the gene in end-organs affected by diabetes. 2) Hohman, et al., (Hohman, T. C., et al., Diabetologia 38(S1):A237 (1995)) recently reported that the levels of AR protein in erythrocytes were one-third the levels in peripheral nerve biopsies of the same diabetic patients (10.75±0.5 μg/Hb vs. 39.0+5.3 μg/protein in nerve) concluding that erythrocyte AR protein levels are not necessarily predictive of those found in target tissues of long-term complications. 3) Blood elements cannot be serially cultured as can fibroblasts which grow easily in culture. 4) Cultured skin fibroblasts retain their in vivo phenotype in tissue culture and therefore provide a good model to use in the study of cellular and genetic perturbations from diabetes.

EXPERIMENTAL DESIGN AND METHOD

A comparison is made of three groups of subjects: non-diabetics, diabetics with no diabetic retinopathy (DR−) and diabetics with diabetic retinopathy (DR+) as defined below in the Inclusion/Exclusion Criteria. The main analytical objective of the invention is to determine and compare across these three groups the levels of AR mRNA, AR activity and sorbitol production in cultured skin fibroblasts and AR activity in erythrocytes. The comparisons are between diabetics and non-diabetics and between DR− and DR+ diabetics. The secondary aims are to determine the correlation between AR mRNA, AR activity and sorbitol production in fibroblasts grown in 5 mM or 20 mM glucose and the correlation of AR activity in fibroblasts with AR activity in erythrocytes. In addition, to quantitate the changes within individuals of each group in the levels of AR mRNA, AR activity and sorbitol in the presence of pathophysiologic levels of glucose (20 mM) are compared to normal physiological levels of glucose (5 mM).

Study Population

Study subjects are recruited from 5 primary care practices in Northern Lower Michigan and the Upper Peninsula of Michigan which are part of the Upper Peninsula Research Network (UPRNET) a primary care research and medical education network which care for approximately 15,500 patients (see letters of support of participants). The populations in the counties of these practices are over 97% white and are slightly older than the average population of Michigan. (The investigators are aware of the predominance of Caucasians in this population and will expand the ethnic diversity in a future expanded and longitudinal NIH funded study application.) Given the age distribution in these counties we expect approximately 700 NIDDM subjects between the ages of 40 and 75 in the patients served by these five practices (Experimental Population Estimates by Age, Sex and County of Residence, Michigan Residents, 1994. Office of the State Demographer, Michigan Department of Management and Budget.). Using age-specific rates of retinopathy from the Wisconsin Epidemiological Study of Retinopathy for this population, it is expected that approximately half (350) to have any retinopathy (NIH Publication No. 95-1468. pp. 67, 310 (1995)). From this data, it was estimated that the required number of patients can be accrued over the three year period of this application.

Recruitment Strategy

Based on power calculations (see Power Considerations below), 100 NIDDM subjects and 50 non-diabetic subjects are recruited. Although this number is adequate for unstratified analyses an unselected diabetic population could yield too few subjects in certain strata or cells, to allow adequate control for potential confounders. Therefore subjects form the pool of diabetics as recruited to ensure sufficient numbers in each of the key cells. Approximately half of the NIDDM subjects are expected to have retinopathy (NIH Publication No. 95-1468 pp. 67, 310 (1995), 37% to use insulin and 28% to have diabetes of longer than 14 years duration. Both insulin use and duration of diabetes are associated with a higher prevalence of diabetic retinopathy (Klein, R., et al., Arch. Ophthalmol 107:244–49 (1989); and Klein, R., et al., Blackwell Scientific Publications, Boston, Chapter 1, p. 1–53 (1992)). To ensure adequate numbers of subjects in each cell to perform multivariate analysis, a periodical check of the distributions of these two variables in the populations recruited is made and recruitment criteria are adjusted to fill specific cells of use/no use of insulin and <15 ≧15 years since diagnosis of diabetes. Since retinopathy is determined at recruitment (see Data Collection below), recruit subjects are selected with or without retinopathy in each of these cells based on information that is available in the chart that will predict who may be more or less likely to have retinopathy prior to enrollment into the study. Non-diabetic subjects are recruited after enrollment is initiated of NIDDM subjects. Non-diabetic subjects are recruited to approximately mirror the age and sex distribution of the NIDDM group.

Subject Recruitment

Subjects with NIDDM

The study begins with the identification and recruitment of eligible diabetic subjects. Each day in each practice the participating research coordinator (already designated in the UPRNET clinics) will scan the scheduled patients charts to determine if the person is diagnosed as having NIDDM. When a NIDDM subject is identified, the nurse inserts a form into their chart notifying the health care provider of their possible eligibility and stating the initial exclusion criterion for the study (see inclusion/exclusion criterion below). The physician will use information in the chart to determine if the patient meets the National Diabetes Data Group definition of Type II diabetes. Duration of diabetes will be determined from chart review including history at diagnosis, chronology of any fasting blood glucose or previous glucose tolerance testing values obtained prior to the diagnosis of diabetes. At the end of the office visit, the health care provider will ask patients that meet the eligibility criterion if they would be interested in participating in the study and obtain informed consent. Patients willing to participate will be asked about their family history of diabetes and retinal disease. A skin forearm biopsy and blood draw are performed by a physician. The physician's office schedules an appointment for the patient with the most conveniently located ophthalmologist for retinal photographs and exam. Subjects will be compensated upon receipt of the eye exam results.

Non-diabetics

Subjects who are not identified as having diabetes or glucose intolerance on their charts and are of the same gender and approximate age to match the distribution in the NIDDM population recruited thus far, are identified and chart flagged at their office visits. At the end of the office visit, the health care provider asks patients that met the eligibility criterion for controls, if they would be interested in participating in the study and describe the study and answer questions. Patients wishing to participate will be asked about their family history of diabetes and retinal disease and be asked to sign an informed consent detailing the benefits and risks of participating in the study. A skin forearm biopsy and blood draw is performed by a physician. An appointment is scheduled by the physician's office with a certified pathology laboratory for a 2 hour oral glucose tolerance test (OGTT) to be certain the subject does not have glucose intolerance or frank diabetes. The appointment time will be recorded on the data log. Subjects are paid upon receipt of the OGTT results. If a person is found to have an abnormal OGTT by National Diabetes Data Group criterion and classified as having diabetes, they will be contacted by the Escanaba office and invited to undergo the exam for retinopathy and medical evaluation for treatment of diabetes. The remaining non-diabetic subjects will serve as controls. If the 2 hour OGTT exclusion alters the distribution of gender and age in control, selective recruitment of controls in specific age-gender strata will be undertaken to balance the control distribution.

Recruitment log

For each attempt at recruitment the physician keeps a log of the patients entry into the study, refusal or exclusion. This log records key variables such as age, gender, duration of diabetes, insulin status, major co-morbidity and reason for non-recruitment (e.g. exclusion criterion, not needed as stratum complete). This allows for contextualization of the sample within the universe of subjects with NIDDM or not having diabetes from which they were recruited and to assess the representativeness for all diabetics or non-diabetics in the source population.

Inclusion/Exclusion Criterion

Overall Initial Criterion

Each person in both the NIDDM and non-NIDDM groups must be between 40–74 years of age, speak English and be judged physically capable by the health care provider of participating in the study. Patients are excluded if they are known to be HIV positive, are currently receiving treatment for a malignancy or have known bleeding disorders, atopy to midriatics, or glaucoma.

Diabetic patients without retinopathy. To be classified as having NIDDM the patient must meet the National Diabetes Data Group definitions for the diagnosis of diabetes mellitus. This is determined by the health care provider reviewing the chart after the initial criterion are satisfied and before recruitment into the study. Patients are not excluded from the study because of the presence of diabetic complications other than retinopathy. Patients with a cataract that precludes photography of the retina will be recruited but set aside from this study because retinopathy status cannot be classified by the protocol. They will be potentially eligible for other studies. NIDDM subjects will be considered to have no retinopathy if they have absence of retinopathy by grading of the retinal fundus photographs.

Diabetic patients with retinopathy

The same criterion is used as above for diabetic patients without retinopathy except that these patients will have any level of retinopathy as determined by the grading of retinal fundus photographs. Patients who have previously undergone photocoagulation is assumed to have "any retinopathy" but are not graded by retinal fundus photographs unless chart review can provide pre-laser therapy phonographs.

Non-diabetics Subjects

Because up to one-half of subjects with diabetes or impaired glucose tolerance have not been diagnosed with diabetes each potential control subject undergoes a 2 hour oral glucose tolerance test to determine the absence or presence of impaired glucose tolerance or frank diabetes according to the criteria set forth by the National Diabetes Data Group. People with impaired glucose tolerance or diabetes are excluded from the non-diabetic group. Subjects who discover they have diabetes as a result of the OGTT are offered the eye exam and included in one of the two diabetic groups. Because subjects with NIDDM potentially have hypertension, cardiovascular, or kidney disease; presence of these conditions in non-diabetes control subjects are not criteria for exclusion from the study.

Data Collection

Physician interview of the patient and record of Patients biopsy, eye or oral glucose tolerance appointment Upon recruitment into the study the physician asks the patient if they have any first degree relatives with diabetes and what age they were diagnosed. He also asks if the first degree relatives have a history of retinal or renal disease. The presence of a family history for retinal or renal disease may be a risk factor for the development of these complications in subjects with diabetes (Genuth, S., et al., Diabetes: 45sup2:31A (1966)). This information is recorded on the form used to flag the chart and will be sent with the chart audit to the UPRNET Research coordinator in Escanaba, Mich.

Chart Audit

Chart review and abstraction for all study subjects is performed by a health care provider at each practice. The data collected includes from the most recent visit: age, weight, height, blood pressure, current medications, and currently active diagnosis which will include presence or absence of kidney disease. For NIDDM subjects, additional information is collected including age at diagnosis of diabetes, criterion used to determine NIDDM, current diabetes therapy (diet, oral hyperglycemic agents, insulin, or combination of these) and date and values of past glycosylated hemoglobin. An attempt is made to calculate "glycohemoglobin months" as a measure of glycemic burden, this may be a useful indication of duration and severity of diabetes. The data log form is currently under development in conjunction with the participating UPRNET clinical practice sites. Upon completion this form is sent to the UPRNET Research Coordinator for data verification and entry.

Forearm punch biopsy

A 3 mm forearm punch biopsy of skin is obtained (using universal precautions) from each subject by the UPRNET participating physician. Each sample is placed in a 14 ml tissue culture tube containing Hams F-12 media with 10% fetal calf serum and 1% penicillin and streptomycin. The sample is placed on ice and shipped by overnight delivery to a laboratory at Michigan State University in East Lansing, Mich. Fibroblasts are cultured, assayed and stored as described below.

Peripheral venous blood phlebotomy

Each study subject has 9 cc of whole venous blood drawn and divided into three, 3 ml aliquots each of which will be used for glycosylated hemoglobin, lipid profile and aldose reductase activity measurements.

Oral glucose tolerance test (non-diabetics only)

This was obtained by a certified pathology laboratory. Results were sent to the referring physician and to the UPRNET research coordinator in Escanaba, Mich.

Glycosylated $HBg_{Al-C}$ and Lipid Profile

Glycosylated hemoglobin Al-C determinations are made from EDTA-treated whole blood using an Abbott Laboratories IMX ion-capture analyzer and a normal reference range of 4.4%–6.4%. lipid profiles will be obtained from serum and will include total cholesterol, triglycerides, HDL, LDL and calculated VLDL measurements using standard enzymatic-assay following phosphotungstinate precipitation of HDLs. All values are reported using age/gender appropriate normal values. Interassay and intra-assay variance are maintained to less than 5%.

Determination of presence of retinopathy (diabetics only)

Diabetic study subjects are scheduled for a retinal photograph with an ophthalmologist at the time of the forearm punch biopsy. Color, stereoscopic fundus photographs are obtained through a dilated pupil from each eye of study subjects by an ophthalmologist participating with the UPRNET. Notification of the results are sent to the patient's physician and negatives were sent to the UPRNET Research Coordinator. Batches of slides are sent for evaluation of the absence or presence and degree of diabetic retinopathy using the Early Treatment Diabetic Retinopathy Study (ETDRS) protocol (Ophthalmology 98::786–806 (1991)). The level of retinopathy are determined for each patient according to the ETDRS interim scale and assigned as background retinopathy, preproliferative retinopathy, or proliferative retinopathy. The results are sent to the UPRNET Research Coordinator.

Determination of levels of AR mRNA, AR activity and sorbitol from a punch biopsy of skin fibroblasts Culture of skin fibroblast. Fibroblast is passaged in culture (using universal precautions) at 37° C. in 5% $O_2$ for three passages, permitting adequate numbers of cells to be grown for isolation of total RNA and determination of AR activity and sorbitol levels. Cells are grown in normal glucose containing media (5 mM glucose), and pathophysiological levels of glucose (20 mM glucose) containing media for up to 4 days. RNA is extracted after 48 hours in culture media containing high or low glucose and AR activity and sorbitol content is determined after 4 days. Fibroblast is indexed and frozen in Ham's F-12 media containing 10% DMSO, 10% fetal calf serum, and 1% penn/strep and stored in liquid nitrogen and cryogenic vials. Frozen fibroblast can be used for analysis of their DNA. All samples are identifiable by only the subject's study number.

Isolation of RNA and quantitation of AR mRNA by filter hybridization

The use of mRNA for analysis of genetic expression is reasonable. The experimental design of this invention requires that a large number of RNA samples be analyzed. In order to rapidly obtain sufficient RNA, a modification of the acid phenol extraction method has been developed (Henry, D. N., et al., J. Clin. Invest. 92(2):617–623 (1993)). This procedure yields, in 8 hours, approximately 100–150 µg of total RNA from confluent monolayers of fibroblast grown in 150 cm² plates, an amount sufficient to perform at least 10 Northern blots or dot blots per data point. 10 µg of total RNA is resolved on denaturing 2.2 M formaldehyde-1% agarose and stained with ethidium bromide to examine the integrity of the RNA. Once integrity of RNA is determined, dot blot analysis is performed with serial dilutions of RNA, applied to ZetaBind (Meridien Conn.) filters with the aid of a vacuum manifold. The filters are fixed and hybridized at high stringency according to the protocol of Church and Gilbert. Human AR and chicken β-actin cDNA probes are labeled with $^{32}$P-dCTP using random primers to a specific activity of $10^9$ dpm/µg and separated from unincorporated nucleotides by gel filtration. After 18 hours, hybridized filters are washed at high stringency. AR and β-actin probes were used on dot-blot analysis because they each hybridize to a single-respective RNA transcript by Northern analysis. Autoradiograms were obtained using multiple exposures in order to remain within the linear range of the film. Autoradiograms were quantitated by high resolution scanning densitometry using an AGFA (Mortel, Belgium) high resolution scanner and NIH image software. Each blot was serially hybridized with human AR and chicken β-actin cDNA probes after stripping filters until free of radioactivity and checked by autoradiography prior to rehybridization with the next cDNA probe. AR and β-actin mRNA levels on different dot blots are comparatively normalized to a common source of total RNA on each blot.

Determination of fibroblast AR activity and sorbitol content

AR2 protein activity is measured spectrophotometrically at 340 nm using 10 mM DL-glyceraldehyde as substrate and expressed as the amount of NADPH that was oxidized per mg protein per minute at 30° C. Sorbitol content is determined enzymatically using sorbitol dehydrogenase method and NAD as substrate. Production of sorbitol is determined by measuring the NADH formed at 37° C. at 455 nm. Sorbitol content is reported as the amount of NADH formed per mg protein per minute.

Analysis of AR expression. (mRNA, activity and sorbitol content) is performed concomitantly from triplicate cultures of each subject. In order to control for interassay variance, 10% of samples undergoes repetitive measure of mRNA analysis, activity and sorbitol content. Interassay variance is monitored by repeating mRNA, activity and sorbitol content assays from thawed fibroblast grown in culture. Intra-assay and inter-assay variance is limited to 10% of the mean for each analysis.

Study Coordination

UPRNET is part of the College of Human Medicine at Michigan State University. Since 1988, the UPRNET has successfully conducted funded research resulting in twenty-six publications. Since 1991, the UPRNET has been awarded twelve research grants from Federal, State and not for profit organizations. Each of the participating UPRNET practice sites is linked by computer, modem, and dedicated bulletin board to each other permitting successful acquisition and transmission of data to the Escanaba campus for analysis. The principal investigator (PI) has presented drafts of this research proposal to the participating members of the UPRNET during its March 1996 convocation in Escanaba, Mich. Members of the UPRNET steering committee and research support group have met monthly with the PI for on-going development of this application.

The UPRNET research coordination center tracks the number of people recruited into each group, the completion of the eye exam for diabetics and the oral glucose tolerance testing for non-diabetics. They will contact people who have missed eye or oral glucose tolerance test appointments and reschedule them if necessary.

Data entry: Data is double entered in a data base program with screens designed to match the data collection forms. All subject derived data is entered by the research support staff at the UPRNET offices in Escanaba, Mich.

Data Analysis

Comparison Across Subject Groups

Standard statistical methods are used to analyze the data gathered. For overall comparison of the three groups, an analysis of variance will be used. The primary comparisons are between non-diabetics and DR−, and DR− and DR+. Generally, t-tests are used for comparing the means of continuous variables and chi-squared tests for comparing the distributions of discrete variables. Continuous variables can be transformed before application of method that require, for their validity, approximate normality of their underlying distributions. Or alternatively, corresponding nonparametric methods will be considered. All testing is two-sided at a significance level of 5%. Where multiple outcomes are compared, control of Type I error are made using appropriate multivariate tests or the Bonferroni method. Initially the non-diabetics, DR− and DR+ groups are compared across a variety of clinical and demographic characteristics. These include AR mRNA, AR activity and sorbitol content in cultured skin fibroblasts, age, gender, presence of kidney disease, and for diabetics, duration of diabetes, use of insulin and level of glycosylated hemoglobin. By design the groups should be balanced with respect to use of insulin and duration of diabetes. Where important differences are detected in variables that are known or suspected of influencing primary outcomes, they are controlled for in the subsequent analysis by regression methods or analysis of covariance, as appropriate. To guard against inflation of the Type I error rate due to multiple comparisons, a multivariate approach will be taken initially by regarding the primary outcomes of AR mRNA ($Y_1$), AR-activity ($Y_2$), and sorbitol production ($Y_3$) in fibroblasts and AR activity in erythrocytes ($Y_4$) as a four-component vector of outcome measures, $Y=(Y_1, Y_2, Y_3, Y_4)$. The dependence of its mean vector is modeled $E(Y|x)=\mu(x)$ on covariates by $\mu=x'\beta$ so where β are regression coefficients on which inference is sought. The covariates x includes the indicator variables for group membership (non-diabetic, DR+ and DR−), for age, duration of diabetes (less than/greater than or equal to 15 years), use of insulin and presence of other diabetic complications. Interactions between these factors are explored. The primary null hypothesis of no difference in the covariate-adjusted mean levels of Y across the three patient groups can be formulated in the statistical model presented here as linear contrasts in the B-coefficients corresponding to the indicator variables for group membership. Logistic regression analysis is used to assess the influence of AR levels (and other covariates such as use of insulin, duration of diabetes, level of glycosylated hemoglobin) on the likelihood of diabetic retinopathy in the subgroup of diabetic patients.

Analysis of relationships within subjects for AR mRNA and activity in 5 and 20 mM glucose Previous work in RPE cells and RBC's (Henry, D. N., et al., J. Clinical Invest. 92(2):617–623 (1993); and Nishimura C., et al., Diabetologia 37:328–330 (1994)) have shown a strong correlation between AR mRNA and AR activity and between AR protein levels and AR activity. To test if these correlations exist in cultured skin fibroblasts grown in 5 or 20 mM glucose the levels AR mRNA, AR activity and sorbitol content are compared in fibroblasts within subjects from the non-diabetic, DR− and DR+ groups. Tests are conducted within subjects to determine if the levels of AR activity in fibroblasts are correlated with those in erythrocytes. Increases in the susceptibility to retinopathy can be caused by a constitutive overexpression of AR (i.e., unregulated by glucose and high at 5 mM glucose) or to a sensitivity to induction of AR mRNA or AR activity by pathophysiological levels of glucose (20 mM). If there are differences in the levels of inducibility of AR RNA or AR activity by 20 mM glucose within subjects in the non-diabetic, DR− and DR+ groups are tested. Analysis of the data after stratification for low/high AR mRNA or activity in 5 mM glucose is made to determine if there is a difference in inducibility of AR mRNA or activity in 20 mM glucose for people with different basal levels of AR expression. All analysis will be carried out on Pentium class PC's using SAS software (SAS Institute, Inc., Cary, N.C.).

Sample Size and Power

The number of participants that were needed for the investigation have been determined by considerations of adequate power to detect differences in key outcome measures in the three groups. Comparison of AR mRNA between groups DR− and DR+ (Groups II and III) were the first focus. If there is a need to detect a difference d in its mean levels between two groups with power $1-\gamma$ using a two-sided test at significance level $\alpha$. Assuming the underlying measures of AR mRNA are normally distributed with standard deviations $\sigma_2$, $\sigma_3$ and the accrual of an equal number of n participants to each group, n is given by $n=(t_{1-\alpha/2}+t_{1-\gamma})^2(\sigma_2^2+\sigma_3^2)/d^2$ where $t_p=t_p(2n-2)$ denotes the p-th percentile of the t-distribution.

Assume $\alpha=0.05$ and $\gamma=0.10$ (that is, power of 90%). Therefore to calculate n values for d and $\sigma_2$, $\sigma_3$ need to be identified. The table below summarizes findings by Nishimura et al (1994) and Hamada et al (1991) on AR protein and activity, respectively. The first article examined AR protein levels and diabetic retinopathy in NIDDM patients which approximates the patients who are DR− and DR+. Standard deviations (SD) are calculated from their results, and from the aforementioned formula computed the sample size n that would be needed to detect the same difference in mean levels as reported. This yielded n=31 for the ratio of 1.33(=4.89/3.68) in the DR+/DR− means. Hamada et al measured AR activity form erythrocytes in three groups of subjects that approximate those of interest: non-diabetics, diabetics with no complications (Hamada did not study diabetics with only no retinopathy and to have this group has been as a substitute for DR−), and diabetics with retinopathy (DR+).

TABLE I

Table: AR levels from published studies

| Group | n | mean | SEM | SD | Source |
|---|---|---|---|---|---|
| DR− | 15 | 3.68 | 0.23 | 0.8908 | Nishimura et al |
| DR+ | 23 | 4.89 | 0.38 | 1.8224 | (AR protein) |
| Non-diabetics | 21 | 5.66 | 0.19 | 0.8707 | Hamada etal |
| Diabetics* | 43 | 6.58 | 0.26 | 1.7049 | (AR activity) |
| DR+ | 17 | 8.43 | 0.49 | 2.0203 | |

*without any complications; SEM = standard error of mean.

Similar calculations to those above were carried out using Hamada's data for comparisons of non-diabetics to diabetics with no complications, non-diabetics to DR+ and diabetics with no complications to DR+. To detect the observed 16% increase in AR activity in diabetics with no complications compared to non-diabetics, approximately 48 subjects are needed. Fewer subjects would be needed to detect the observed differences between non-diabetics and DR+ (8 subjects) and between diabetics with no complications and DR+ (23 subjects) because the differences are larger. Both Nishimura and Hamada used erythrocytes for their determination of AR activity or protein levels. The present invention uses both erythrocytes and fibroblasts. A conservative approach is chosen to ensure that there is sufficient power to detect differences in AR levels between the groups if they turn out to be smaller than expected from the work on erythrocytes. The sample size of 50 per group gives us sufficient power (>90%) to detect differences in AR protein level of at least 25% in erythrocytes between diabetics with and without retinopathy based on the work from Nishimura.

The mechanism(s) regulating aldose reductase (AR, EC.1.1.1.21) gene expression are characterized in cells from tissues involved in the complications of diabetes. AR appears to have a role in the genesis of the chronic complications of diabetes, and there is growing evidence that AR participates in, and is modulated by, physiological osmoregulation. The retinal pigment epithelium (RPE) supports and nourishes the neuroretinal cells in vivo. They exhibit glucose-induced, AR inhibitor-sensitive physiological impairment manifested by deterioration of electroretinograms in vivo and decreased rod outer segment phagocytosis in vitro that is prevented by AR inhibitors. Immunohistochemical data suggest that AR protein is more abundant in RPE cells of patients with background or proliferative retinopathy. Thus RPE cells constitute an appropriate pathophysiologically relevant model in which to assess the effects of AR gene expression and polyol metabolism.

The polyol hypothesis asserts that diabetic complications (such as retinopathy, neuropathy and nephropathy) result, in part, from the direct or indirect consequences of sorbitol production from glucose by AR, a member of the monomeric, NADPH-dependent aldoketoreductase family. Despite its pivotal role in the polyol hypothesis, little is known about the regulation of AR gene expression. Preliminary studies have examined the change in AR mRNA in cultured RPE cells subjected to hyperosmotic media. Of the four RPE cell lines originally studied, three demonstrated this "normal" AR induction in response to osmotic stress, but a fourth (RPE 91) exhibited constitutive high level expression of AR mRNA and accelerated and exaggerated accumulation of sorbitol. Aberrant expression of AR such as that exhibited by this fourth RPE cell line, predisposes the patient to the development of diabetic complications.

The research on RPE cells is as follows:

1) To quantitate the change in the steady-state AR mRNA level in RPE cells in response to exposure to glucose, 3-O-methylglucose and mannitol and to correlate the mRNA levels with changes in AR protein and sorbitol.
2) To determine whether alterations in AR gene transcription, and/or mRNA stability cause the changes in steady-state AR mRNA level.
3) To characterize the promoter of the AR gene, and identify the cis-acting regulatory sequences which regulate osmotic induction of transcription.
4) To determine the mechanism of aberrant AR expression in RPE 91.

Isolation, characterization and maintenance of RPE cells in vitro. RPE cells are non-transformed cells, easily isolated from postmortem eyes, which retain well defined phenotypic characteristics for up to 30–40 passages in culture (Ben, D., et al., Diabetes 44:727–732 (1995)). The retinal pigment epithelium represents a homogeneous monolayer of cells that have a nutritive and supportive role for the neuroretinal in vivo. Furthermore, they exhibit glucose-induced MI depletion in vivo (Patell, A., et al., Polymorphisms of the Aldose Reductase (ALR2) Locus and Susceptibility to Diabetic Microvascular Complications. Enzymology and Molecular Biology of Carbonyl Metabolism 4. H. Weine, Ed. Plenum Press, N.Y. pp.325–332 (1993)) and in vitro (Ben, D., et al., Diabetes 44:727–732 (1995)) that is associated in both cases with AR2 inhibitor or MI-sensitive physiological impairment such as decrease rod outer segment phagocytosis (Ben, D., et al., Diabetes 44:727–732 (1995)) or deterioration of electroretinograms (Patell, A., et al., Enzymology and Molecular Biology of Carbonyl Metabolism 4. H. Weine, Ed. Plenum Press, N.Y. pp.325–332 (1993)). Thus RPE cells in vitro constitute an appropriate pathophysiologically relevant model in which to assess the effects elevated glucose has on polyol metabolism and AR2 gene expression. Primary cultures of RPE cells are established and maintained by a modification of the method of Del Monte and Maumenee (Ben, D., et al., Diabetes 44:727–732 (1995)). In brief, RPE cells are recovered with fire-polished Pasteur pipettes under direct observation with a dissecting microscope from surgically removed, sagittally bisected, post-mortem eyes obtained from the Michigan Eye Bank within 24 hours of death. These cells are cultured in Hams F-12 nutrient medium containing 16% fetal calf serum, 2 mM glutamine, 100 U/ml penicillin, 100 $\mu$g/ml streptomycin and 0.075?% (w/v) sodium bicarbonate in 35 mm culture dishes incubated at 37° C. for 10 min, centrifuged for 5 min at 50 xg, resuspended in new culture medium and replated. The established RPE cell lines are passaged at a density of 40–100,000 cells/cm$^2$ in 25 cm$^2$ or 75 cm$^2$ flasks in Minimal Essential Medium with 2 mM L-glutamine (MEM) ([MI]=11.1 $\mu$M) containing 20% calf serum (CS) ([MI]=90–120 $\mu$M) and 5 mM glucose at 37° C. in humidified 95% air and 5% $CO_2$. The phenotypic characteristics ar monitored microscopically, functionally (rod outer segment phagocytosis and immunocytochemically (aceto-acetylated LDL receptor protein. All experiments are performed between passages 19–24 of the 4 RPE cell lines whose donors were of similar age and gender (Table 2).

TABLE 2 hRPE CELL LINES

| Number | G | Age | Cause of Death | Date of Death | Hours to Enuc. | Hours to Culture | Passage Number |
|---|---|---|---|---|---|---|---|
| 45 | F | 50 | massive CVA | 2/8/87 | 5.75 | 21 | 21 |
| 91 | F | 54 | cerebral bleed | 4/14/88 | 2.5 | 21 | 19 |
| 0125 | M | 12 | gunshot wound | 3/1/84 | 8 | 22 | 24 |
| 0308 | M | 15 | motor vehicle accident | 10/23/84 | 5 | 14 | 23 |

STUDIES AND RESULTS

Figure 2:
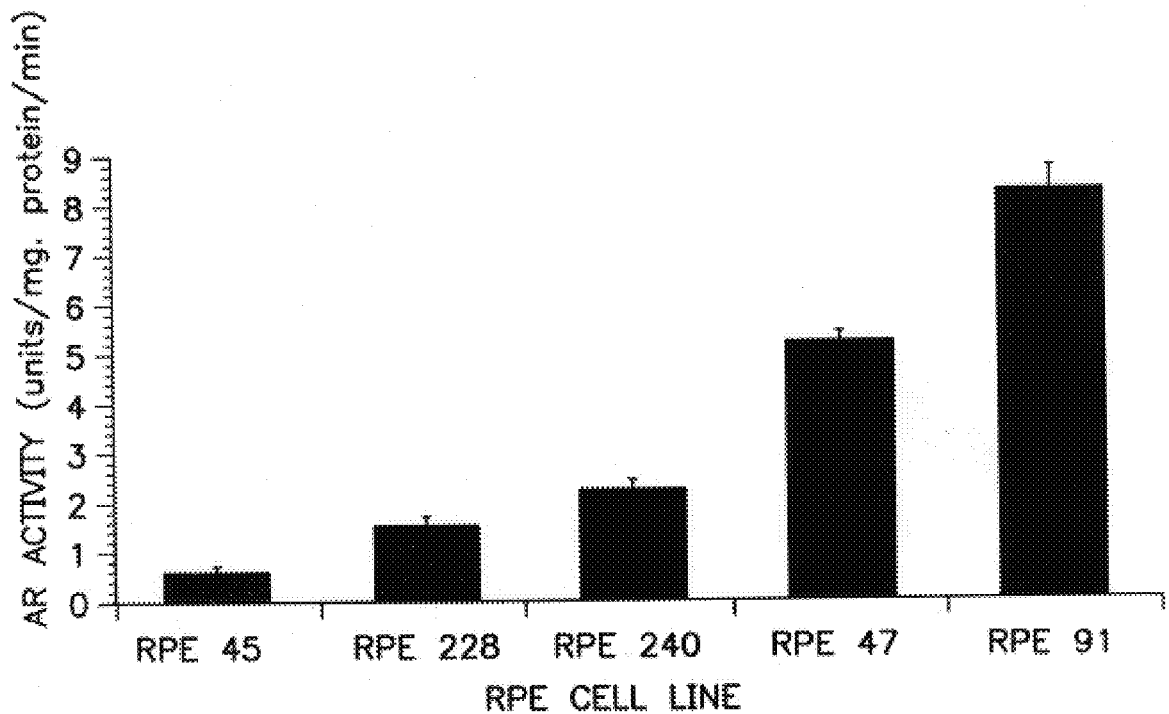
FIG. 2 is a graph showing AR activity in the isolates of FIG. 1 parallels steady state mRNA levels. There is heterogeneity of aldose reductase activity in the different RPE cell lines. Activity was determined by change in $OD_{340}$ of NADPH using glyceraldehyde as substrate in confluent triplicate cultures of RPE cell lines. Standard error bars are indicated.

1) To quantitate the change in the steady-state AR mRNA level in RPE cells in response to exposure to glucose, 3-O-methylglucose and mannitol and to correlate the mRNA levels with changes in AR protein and sorbitol Results were published in the Journal of Clinical Investigation (J. Clin Invest. 92(2) :617–623 (1993), American Journal of Physiology (Am J Physiol. 265(3 pt 1):E428–438) and by oral presentation of the United States-Japan Aldose Reductase Workshop, ("Altered Aldose Reductase Gene Expression and Diabetic Complications. D. N. Henry, D. Larkin, M. J. Stevens, M. Togawa, P. D. Killen, D. A. Greene. Kona, Hi. Feb. 19, 1994). Twenty (20) additional RPE cell isolates were screened to determine their levels of AR gene expression by Northern and dot blot quantitation. Three of these isolates (15%) had steady state levels of AR mRNA which were intermediate in quantity when compared to the RPE 45 (low basal expresser) and RPE 91 (high basal expresser) cell isolates originally described (FIGS. 1 and 2).

Figure 3:
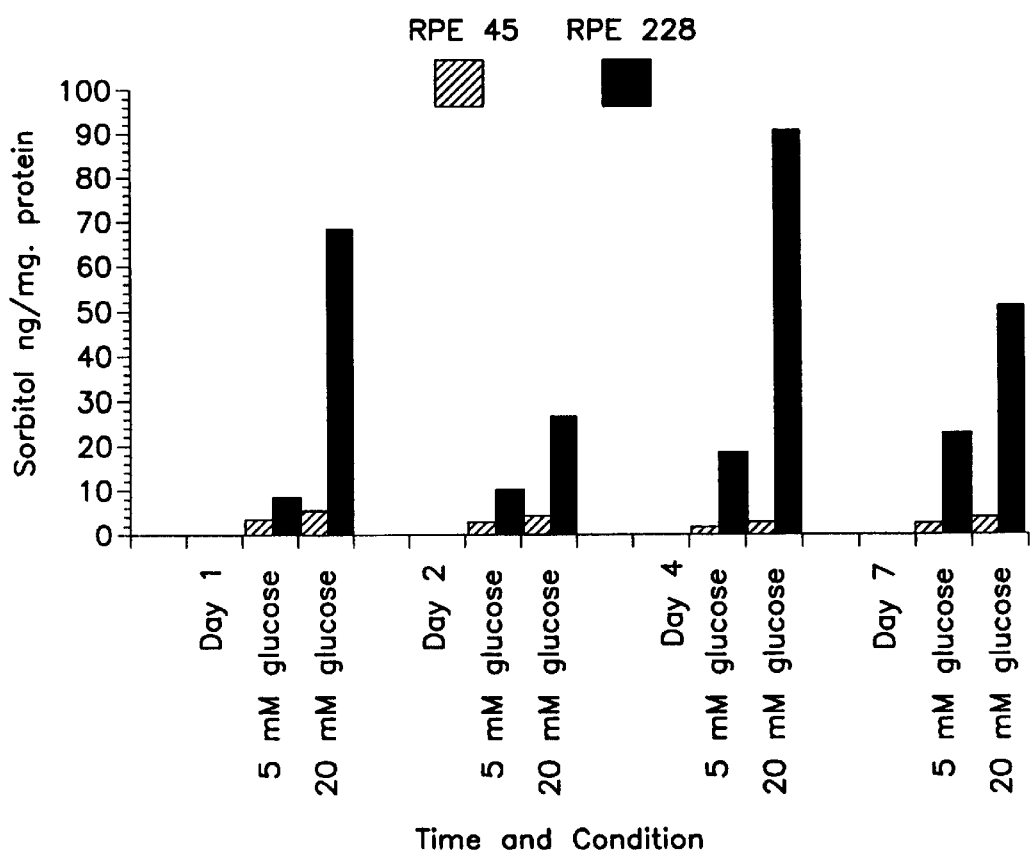
FIG. 3 is a graph showing data from the RPE 45 and RPE 228 cell lines showing that AR activity parallel changes in sorbitol (see FIG. 2). RPE cell line 228 with higher basal AR mRNA and activity produces greater amounts of sorbitol than the RPE cell line 45 with low basal AR expression. Cells grown up to one week in Iso-osmolar (5 mM glucose) or pathophysiologic levels of glucose (20 mM) containing media.

AR activity in these isolates parallels steady state mRNA levels. FIG. 3 shows data from the RPE 45 and RPE 228 cell lines suggest that AR activity parallel changes in sorbitol and myo-inositol (MI). Changes in MI and Sorbitol were measured in RPE cell lines 240 and 47. These data suggest that heterogeneity of AR expression is not unique to the RPE 45 and 91 cell lines. These findings were presented at the Department of Pediatrics 4th Annual Research Symposium on Sep. 23, 1994 (Heterogeneity of Aldose Reductase Gene Expression in Primary Cultures of Human retinal Pigment Epithelial Cells. Tracy Chin, Noelle Sasina, Monte DelMonte, Thommy Thomas, and Douglas Henry). Heterogeneity of AR expression has important physiologic consequences when higher basal AR expression cells are exposed to pathophysiologic levels of glucose. In order to measure AR protein in RPE cells, antibodies against AR were made using a p-Mal fusion protein with a partial length AR cDNA. Rabbits were immunized and titers against the maltose fusion protein were high (1:100,000) but low against the AR protein (1:2–1:6) alone. Another p-Mal-AR fusion protein is being made using a different cDNA for immunization of rabbits and antibody production. A functional full-length AR cDNA has been cloned from a pcDNA1 (Invitrogen, San Diego, Calif., Library Support Guide) with RPE cDNA library. Transient transfections of RPE cell line 45 were performed to determine if this full length AR construct with (pcDNH8; a full length AR clone in pcDNA1) is deposited at Michigan State University, East Lansing, Mich. is functional. The pcDNA1 AR construct appeared to be functional in RPE 45. Control transfections can include a sham transfection as well as a truncated cDNA which lacks the translation initiation site. Data suggest a 3 fold increase in sorbitol production in transfected RPE 45 cell lines using the full length AR cDNA when compared to the sham transfected cells. This construct is used to create stable transfected RPE cell line in order to recapitulate the RPE 91 phenotype for future studies in the physiological consequences of high basal AR expression and aldose reductase inhibitors.

Figure 4A:
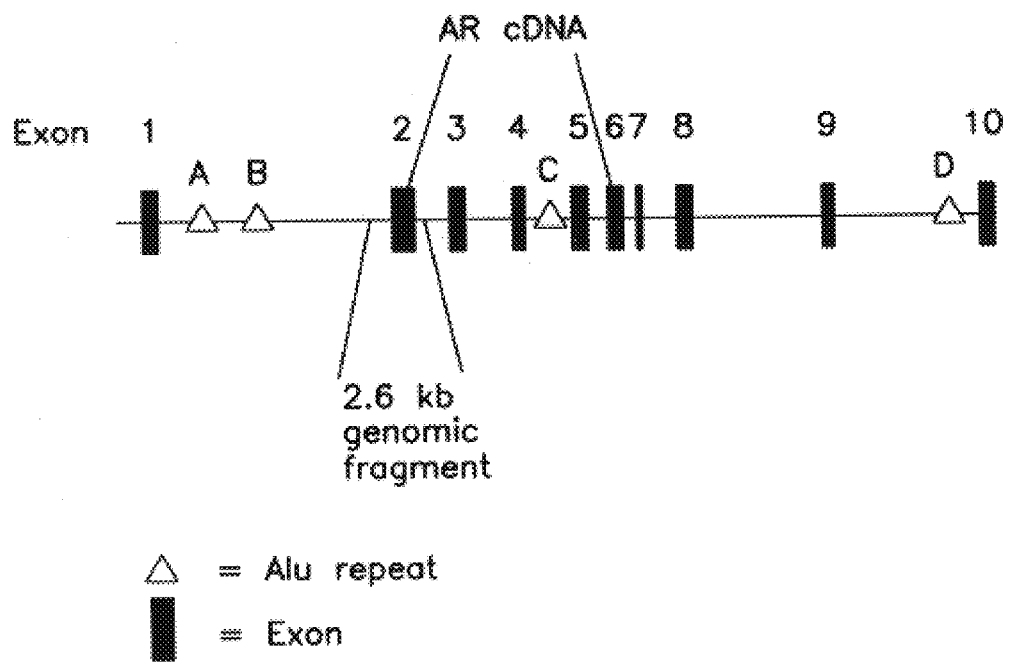
FIG. 4A is a chart showing the structure of human AR gene. Included are AR cDNA and 2.6 Kb genomic fragments used in nuclear run on studies are shown.
Figure 4B:
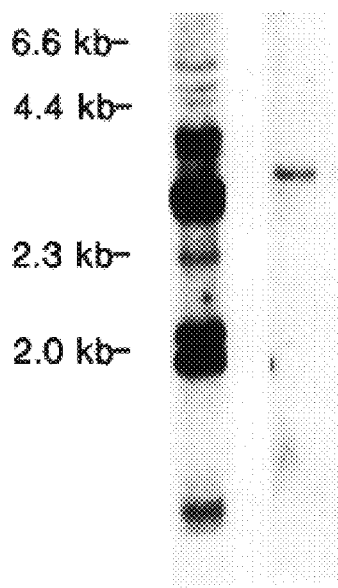
FIG. 4B is a photograph of a southern blot showing an analysis of human RPE genomic DNA. 10 μg of BAMHI digested genomic DNA was resolved by electrophoresis on 1% agarose gels and transferred to nylon filters. The blots were hybridized with the $^{32}$P-labeled AR-cDNA (left) or the AR 2.6 Kb genomic fragment (right). The AR-cDNA hybridized to multiple restriction fragments confirming the presence of multiple pseudogenes. The 2.6 Kb AR genomic fragment hybridized to a single fragment of expected size, and thus could be used as a single copy sequence for assessment of AR gene transcription by nuclear run-on analysis.
Figure 5A:
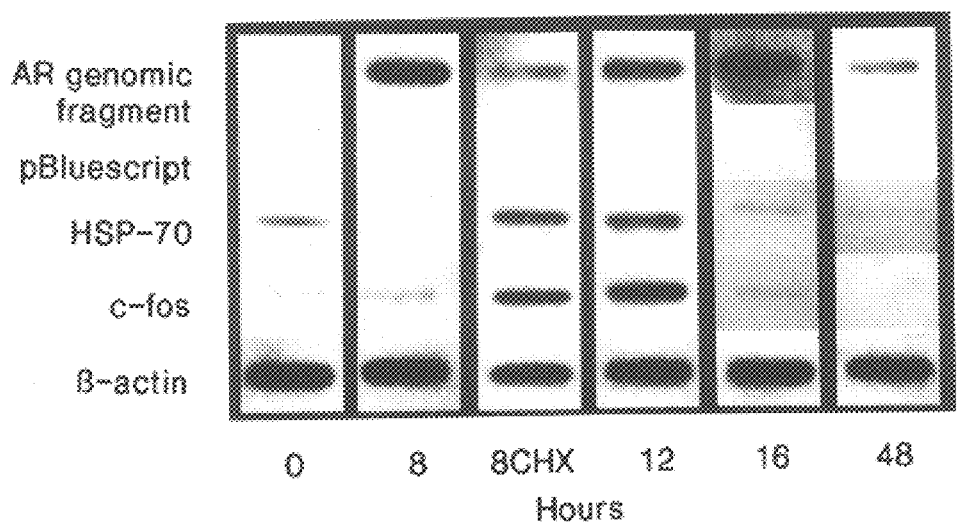
FIG. 5A is a photograph of a gel showing nuclear run-on quantitation of transcription in RPE 45 cell lines. Cells were grown in 300 mM mannitol containing media for up to 48 hours as a hyperosmotic stress. 8 hour time points in mannitol or mannitol plus 10 μg/ml cycloheximide (CHX). CHX inhibited induction of AR gene. As quantitated by the nuclear run-on experiments using the appropriate genomic target, AR transcription began to increase at two hours and was maximal (12 fold) at 12 hours, returning to near basal levels by 48 hours when low basal AR expressing cells (RPE 45) are exposed to hyperosmolar stress (300 mM glucose) (see also FIG. 5B).
Figure 5B:
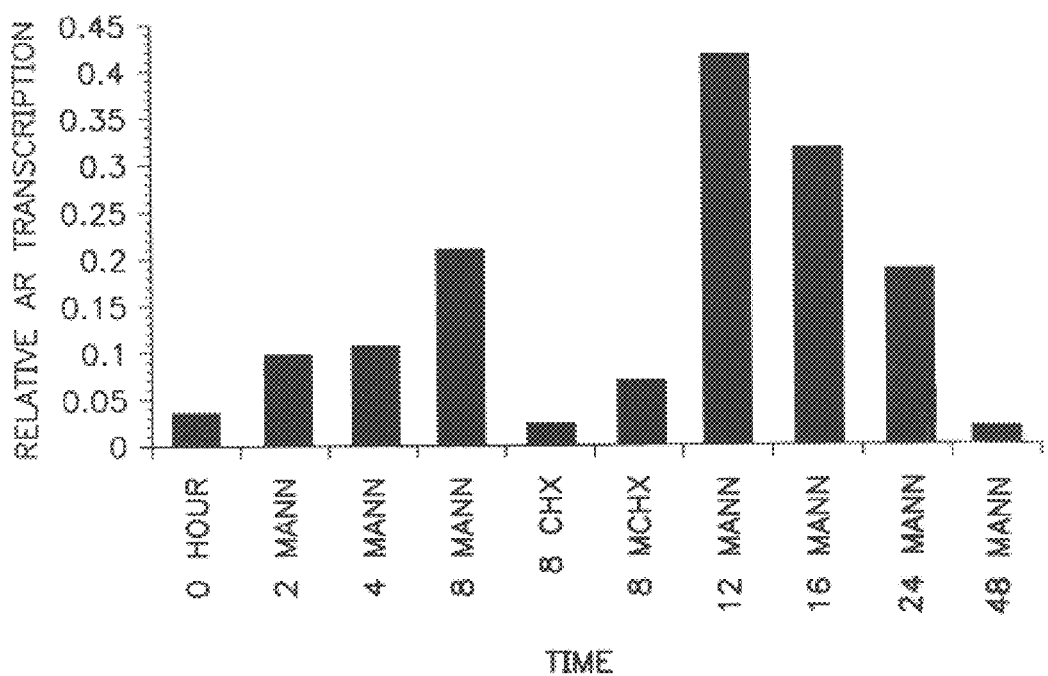
FIG. 5B is a graph showing quantitation of AR transcription in RPE 45 cell line exposed to 300 mM mannitol for up to 48 hours. 300 mM mannitol±10 μg/ml cycloheximide (CHX) at 8 hours exposure. Basal transcription of AR not affected by CHX. Hyperosmolar stress increased transcription but was inhibited by CHX. Osmotic induction of AR transcription was inhibited by treatment with cycloheximide while the basal level of transcription in these cells were not inhibited by cycloheximide (CHX).
Figure 6A:
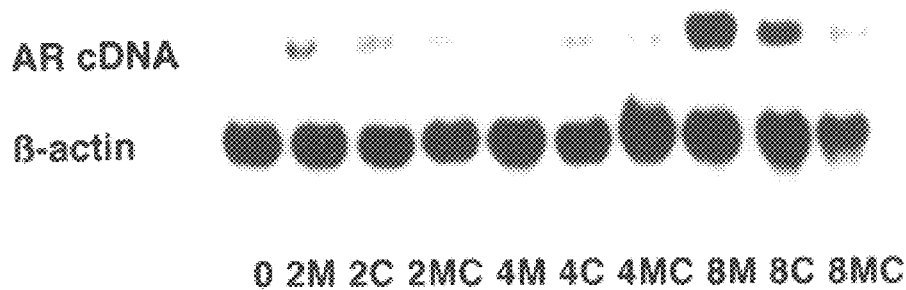
FIG. 6A is a photograph showing a northern blot showing the RPE 45 cell line used in nuclear run-on. Inhibition of AR transcription was not due to toxic effect of cycloheximide (CHX) as transcription of c-fos was increased by cycloheximide (CHX) at same time point. Northern analysis of steady state levels of AR mRNA were 3–5 fold greater in the presence of CHX at 2, 4 and 8 hours (see also FIG. 6B).
Figure 6B:
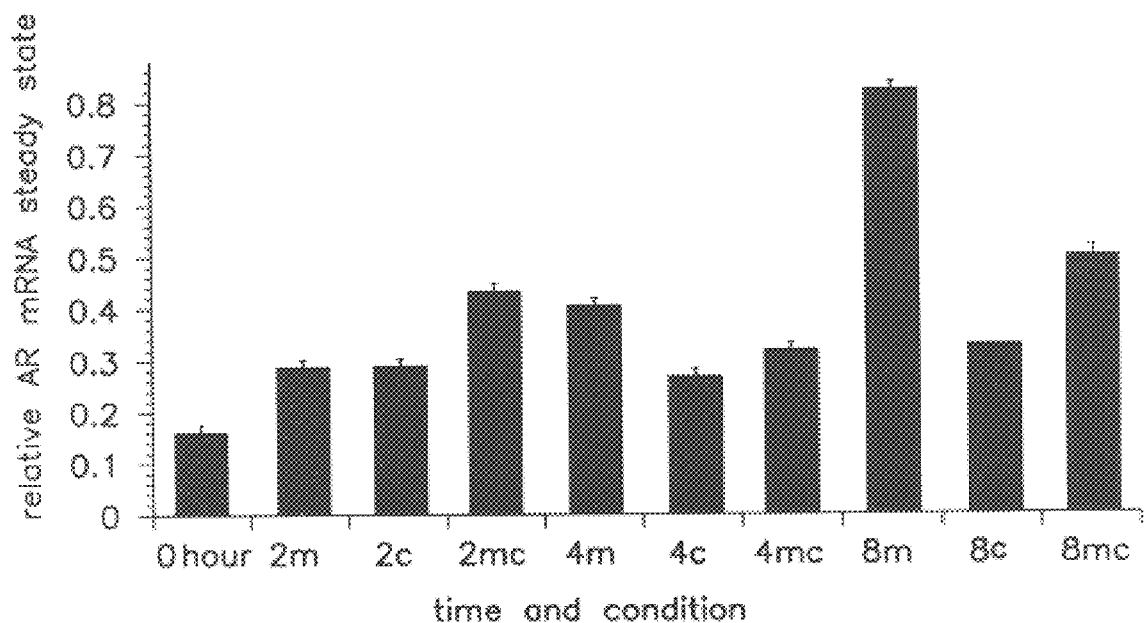
FIG. 6B is a graph showing dot blot quantitation of AR steady state mRNA isolated from companion plates used in nuclear run-on assays. Steady state level of AR mRNA increased by hyperosmolar stress (300 mM mannitol=m) at 2, 4 and 8 hours and by inhibition of protein translation (10 μg/ml cycloheximide=c) at 2, 4 and 8 hours. Mannitol plus cycloheximide (mc) inhibited induction of AR steady state at 4 and 8 hours. Standard Error bars are shown.

To determine whether alterations in AR gene transcription, and/or mRNA stability cause the observed increase in AR mRNA level Results were presented at the American Society of Nephrology annual scientific meeting (Henry, D. N., et al., J. Am. Society of Neph. 4(3):887 (1993)). An AR cDNA cannot be used as a target for nuclear transcription quantitation because of the presence of multiple pseudogenes to which labeled heteronuclear RNA will hybridize. A single genomic AR fragment (proven by Southern hybridization) was used to quantitate osmotic induction of AR transcription in the RPE 45 isolate. The ASR cDNA hybridized to multiple genomic fragments while a BamHI AR genomic fragment hybridized to a single band of expected size, consistent with a single gene (FIGS. 4A and 4B).

To characterize the promoter of the AR2 gene, and identify cis-acting regulatory sequences An osmotically induced enhancer of aldose reductase gene transcription in the 5' untranslated region of the gene has been identified (Shiro Maeda, et al., J. Am. Society of Nephr. 5(3):314 (1994)). This fragment works with both the homologous and a heterologous (thymidine kinase) promotor and was capable of increasing AR gene transcription independent of position and orientation to the promotor. DNA foot-printing and gel-shift assays are being performed to determine the region of the enhancer and what transacting factors may be binding to it's cognate cis-acting element(s).

Figure 7:
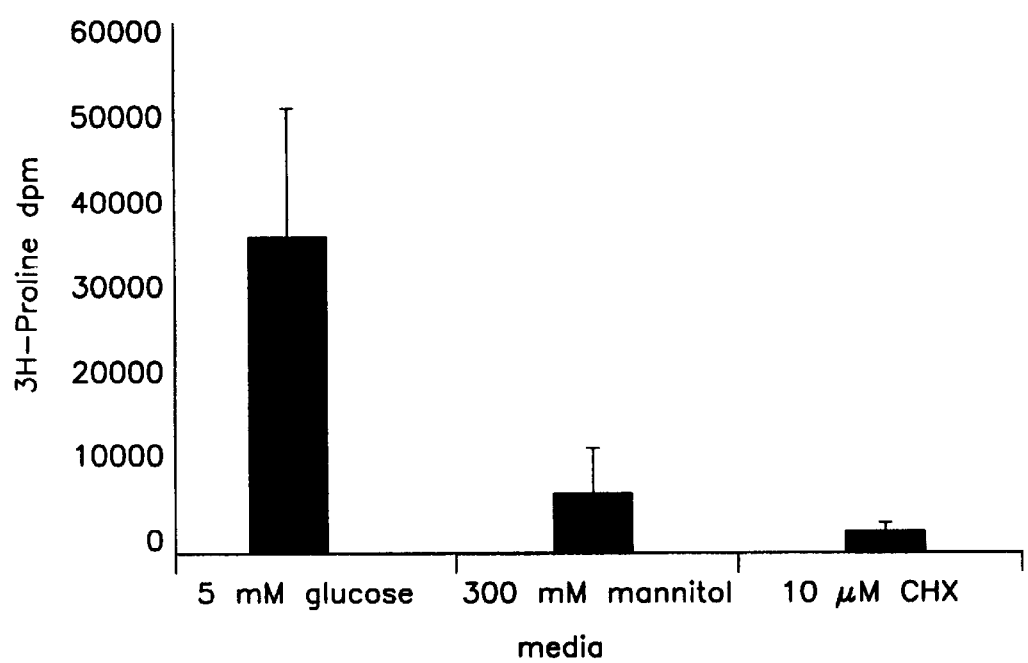
FIG. 7 is a graph showing $^3$H-proline incorporation into RPE 45 cells exposed to hyperosmolar stress (300 mM mannitol) or 10 μg/ml cycloheximide inhibitor. Standard Error bars are shown.

Results of nuclear run-on experiments (FIGS. 5A, 5B, 6A and 6B) have demonstrated that the basal level of transcription of AR in the RPE 91 and RPE 45 cells are similar while steady state mRNA levels are greater in the RPE 91 cell line. Increased steady state levels of AR mRNA in the 91 is most likely due to differences in mRNA half-lives when compared to the RPE 45 cell line. Actinomycin D and steady state labeling of RNA in RPE cells is presently being used to determine the half-lives of the transcripts from RPE 45 and RPE 91 cell lines. Three additional RPE cell lines have been identified (see above) which have intermediate levels of AR expression. It is not known if these cell lines share a common post-transcriptional defect responsible from the greater level of AR mRNA. FIG. 7 shows $H^3$-proline incorporation under various conditions. FIGS. 8A and 8B show proteins under different glucose concentrations.

DISCUSSION

The identification of an osmotically activated enhancer allows specific transacting factors responsible for osmotically induced AR transcription to be determined and is of importance to understanding other osmotically inducible genes (sodium-myo-inositol transporter, taurine transport, betaine transport, and glycerolphosphorylcholine uptake). AR transcription in low basal AR expressing cells appears to have dual regulation; 1). a protein labile component which is necessary for complete induction of AR transcription by osmotic stress, 2). a basal level of transcription independent of protein synthesis. Northern and dot blot quantitation of steady state levels of AR mRNA demonstrated an increase in AR mRNA after osmotic shock, cycloheximide, or both. Osmotic stress in RPE cells inhibited protein translation nearly as well as treatment with cycloheximide alone (87% vs. 98%). Recovery from osmotic stress required the orchestrated response of the cell to permit selective translation of proteins most necessary during osmotic challenge. Accumulation of AR mRNA shortly after (28 hours) treatment with cycloheximide probably occurred by increased stability of the message as AR transcription was not increased by cycloheximide treatment alone. Increased stability of the AR transcript could occur by loss of a protein (osmotic stress and/or cycloheximide inhibit protein translation) regulating AR transcript turn-over. This quality of gene regulation is one mechanism whereby the cell may continue to transcribe AR (and presumably accumulate transcripts or make AR protein) until the cell has recovered enough to permit broader protein translation. In this sense, AR is similar to both an immediate early response gene (c-fos, c-myc, Egr-1, etc.) and a secondary responder dependent on prior protein synthesis for transcription to increase. The discovery of human cell lines (derived from organs which develop end-organ complications from diabetes which over-express the AR gene and produce sorbitol and deplete myo-inositol in response to pathophysiologic levels of glucose, suggest a possible mechanism whereby these individuals are predisposed to the diabetic complications. The early, prospective identification of particular patients prone to particular diabetic complications motivates and justifies intensive prophylactic metabolic intervention. Aberrant constitutive generalized or tissue-specific over-expression of AR in some patients with diabetes mellitus, whether on a genetic or acquired basis, could constitute such a predisposing factor, rendering over-expression of AR in RPE 91 cells provides an invaluable marker for the identification of such patients. The relevance of mRNA stability to pathologic processes is well documented. Spontaneous monocytic tumors in a myc transgenic mouse overproduced CSF (colony stimulating factor 1 principally stimulating the proliferation of stem cells into granulocytes and macrophages). The underlying mechanism was not due to increased transcription but to selective stabilization of the CSF transcript. Enhanced stability was not due to loss of a 67 bp AUUA rich region but hypothesized to be due to increased stability of the transcript due to a tumor specific trans-acting factor (Schuler G. D., et al., Cell 55:1115 (1988)). The proto-oncogene c-fos is normally expressed at low levels but they can rapidly be induced to high levels by viral-fos transformation resulting in the viral transcript having an AU-rich stretch of 67 nucleotides in the 3'-UTR truncated resulting in increased stability when compared to the c-fos untruncated transcript (Curran, T., The fos oncogene. In the Oncogene Handbook, edited by Reedy E. P., Skalka, A. M., Curran, T. p 307. Elsevier, Amsterdam (1988)). Identification of inheritance patterns of a marker, or its acquired association with other putative risk factors for diabetic complications, could provide unique insight into this pathogenetic process, and provide new therapeutic modalities to diminish the risk of diabetic complications through manipulation of AR gene expression. Thus, the ultimate application of this research is in the clinical arena to identify, treat, and perhaps prevent diabetic complications, as well as understand their patient-to-patient variability and pathogenesis. Understanding the mechanisms which regulate AR gene expression in RPE cells represents an important advance not only for investigator interest in retinal cell biology but the response to osmotic stress appears highly conserved in a wide variety of cells and tissues. Thus, the insights gained from the present invention will likely be equally relevant to renal physiologists and nephrologists. The present invention sets the stage for characterization of the trans-acting factors which regulate the cellular response to osmotic stress. This fundamental knowledge will provide the foundation for the design of new therapeutic approaches designed to ameliorate end organ damage. The results observed in the RPE 91 cells are manifested in patients prone to develop diabetic complications. Thus, this invention will find rapid clinical implementation in identifying those patients at risk for development of accelerated complications.

Assessment of AR2 mRNA stability

In order to determine the half-life of AR mRNA, RPE cells are exposed to osmotic stress for various times before the addition of actinomycin D (usually 10 mg/ml, the actual amount to be determined by inhibition of $^3$H-UTP incorporation). Control cultures in isotonic media are similarly treated. RNA is sacrificed at various times following the inhibition of RNA synthesis and quantitated (by filter hybridization of Northerns and serial dilution of RNA in dot blots). Differences in the rate of disappearance would suggest a change in mRNA stability (Harrold, S., et al., Anal Biochem 198:19–29 (1991).

To characterize the promoter of the AR2 gene, and identify cis-acting regulatory sequences An osmotically induced enhancer has been identified in the 5'UTR sequences of the AR gene. A 5' flanking sequence from the −2800 to −600 bp which does not initiate transcription, but enhanced transcription by homologous and heterologous promoters specifically in response to osmotic stress.

The following Examples demonstrate the different phenotypes of aldose reductase (AR) expression as well as the results of nuclear run on experiments to quantitate the rates of transcription for AR among these different phenotypes. Differences in transcription of AR cannot account for the increased steady state levels of AR mRNA seen on Northern analysis. Four different AR phenotypes in primary human RPE cell cultures are described. 1) low basal AR expressors, 2) intermediate AR expressors, 3) high constitutive AR expressors, and 4) those demonstrating inducible AR by pathophysiological levels of glucose.

Creation of cDNA Probes

Human RPE cell total RNA was transcribed using random primers. The product of that transcription was reverse transcribed PCR polymerase using synthetic oligonucleotides SEQ ID NO:3; SEQ ID NO:4; SEQ ID NO:5; and SEQ ID NO:6 specific for either aldose or aldehyde reductase. The products of these reactions were subcloned into pKSM13$^+$ plasmids and sequenced (SEQ ID NO:1 and SEQ ID NO:2). These cDNA's have a high complement with human and rat AR genes.

EXAMPLE 1

These examples show the heterogeneity of AR Expression in different RPE cell isolates.

FIG. 10 shows a blot in a test for steady state levels of AR mRNA by Northern analysis from four different primary cultures of human RPE cell isolates in vitro. Cells were grown in normal (5 mM) and hyperosmolar levels of glucose (300 mM) containing media. Hyperosmolar stress is a known inducer of AR but rarely sustained in diabetes. These data demonstrate three different phenotypes of RPE cells: 1. low basal AR expressors, 2 & 3, intermediate AR expressors, and 4. high constitutive AR expressors. These phenotypes are believed to exist in vivo and would show increased susceptibility to AR related development of long-term complications from diabetes.

EXAMPLE 2

FIG. 11 shows Basal AR protein activity in four different human primary RPE isolates from FIG. 1 grown in normal glucose (5 mM) containing media. AR activity is proportional to the basal levels of AR mRNA expression. Increased expression of the gene (FIG. 10) resulted in higher activity of the protein (FIG. 11). Heterogeneity of AR expression in this model has physiological significance as sorbitol levels parallel AR mRNA and protein activity.

EXAMPLE 3

FIG. 12 is a Northern blot showing induction of AR by pathophysiological level of glucose (20 mM) and hyperosmolar level of glucose (300 mM) in a primary human RPE isolate in vitro. AR activity increased proportionally to the levels of AR mRNA in this isolate. This is the fourth phenotype of AR expresser from human primary cultures of RPE cells.

EXAMPLE 4

FIG. 13 is a Northern blot demonstrating similar basal levels of AR mRNA expression from primary fetal cultures of human RPE cells and scleral fibroblast in vitro. Similar levels of AR expression from these different tissues suggest "peripheral" fibroblast accurately reflect the amount of AR expression in the RPE cell layer.

EXAMPLE 5

FIG. 14 is a Northern blot showing dot blot quantitation of induction of AR by increasing concentrations of glucose in human pancreatic ductal cells (CAPAN-1) in vitro. Cells were grown for 48 hours in media containing increasing concentrations of glucose. Induction of AR is seen as early as 11 mM glucose. Dot blots were easily quantified by scanning densitometry and normalized for loading once blot is stripped of AR cDNA probe and reprobed with β-actin to control for differences in RNA loading. These data further support the possibility of induction of AR by pathophysiological levels of glucose.

EXAMPLE 6

FIG. 9 is a blot nuclear run-on quantitation of AR transcription from high basal AR expressing RPE isolate (RPE-HE) and low basal AR expressing RPE isolate (RPE-LE) normalized to the levels of vimentin transcription in vitro (upper panel). Northern analysis of steady state AR mRNA from the same isolates used for nuclear run-on studies (lower panel). Differences in steady-state AR-mRNA in these isolates are not due to different rates of AR gene transcription but are probably due to different AR mRNA stabilities. Differences in AR mRNA stability may be responsible for higher basal AR expression in some RE isolates.

The examples provide evidence that heterogeneity of AR expression exist in vitro and results in a proportional range of AR activity. Cultured peripheral fibroblast had similar levels of AR expression seen in retinal pigment epithelial cells in vitro. Subtle changes in AR expression can be detected using dot blot hybridization.

It is intended that the foregoing description be only illustrative of the present invention and that the present invention be limited only by the hereinafter appended claims.

I claim:

1. A method of testing cells to determine whether a human diabetic patient has an abnormal aldose reductase RNA expression phenotype which comprises:
   (a) isolating cells from the patient which are indicative of a risk of diabetic complications;
   (b) exposing the cells from the patient to glucose at pathophysiologic levels which can occur commonly in diabetes; and
   (c) determining a level of aldose reductase RNA encoding the aldose reductase in the exposed cells, wherein an elevated level of production of the RNA compared to levels of the RNA in cells not exposed to the glucose at pathophysiologic levels is indicative of the abnormal phenotype.

2. A method for the treatment of a diabetic patient having an abnormal aldose reductase RNA expression phenotype which comprises:
   (a) isolating cells from the patient which are indicative of a risk of diabetic complications;
   (b) exposing the cells isolated from the patient which can be indicative of the risk of diabetic complications to glucose at pathophysiologic levels which can occur commonly in diabetes;
   (c) determining a level of production of aldose reductase RNA encoding the aldose reductase in the exposed cells, wherein an elevated level of the RNA compared to the level of the RNA in cells not exposed to the glucose at pathophysiologic levels is indicative of the abnormal phenotype; and
   (d) treating the patient whose cells have the abnormal phenotype with an inhibitor of the aldose reductase.

3. The method of any one of claims 1 or 2 wherein a probe selectively binds the RNA which is used for determining the level of expression.

4. The method for determining a level of aldose reductase RNA in the cell of either claims 1 or 2 wherein a probe which is selected from the group consisting of a cDNA and a RNA is used to selectively bind the aldose reductase RNA.

5. The method of any one of claims 1 or 2 wherein a DNA or RNA probe which selectively binds a marker RNA in the cells other than the aldose reductase RNA is used as an internal standard.

6. The method of claims 1 or 2 wherein RNA is extracted from the cells and the RNA reverse transcribed to provide a cDNA and wherein an elevated amount of the cDNA is indicative of the elevated level of the aldose reductase gene expression.

7. The method of claim 1 or 2 wherein the cells having the abnormal phenotype are then tested by exposing the cells to the glucose at pathophysiologic levels in the presence of an aldose reductase inhibitor, wherein reduction of the aldose reductase RNA levels in the cells indicates effectiveness of the inhibitor.

8. The method of claim 1 wherein the cells are selected from the group consisting of skin, blood, nerve, renal and eye cells.

9. The method of claim 1 wherein the cells are fibroblasts from skin.

10. A method of treating a diabetic patient having an abnormal aldose reductase RNA expression phenotype which comprises:
   (a) isolating cells from the patient which are indicative of a risk of diabetic complications;
   (b) exposing the cells from the patient to a pathophysiologic concentration of glucose;
   (c) determining a level of aldose reductase RNA encoding the aldose reductase in the cells, wherein production of aldose reductase RNA by the pathophysiologic concentration of glucose is increased compared to the cells not exposed to the glucose at the pathophysiologic concentration is indicative of the abnormal phenotype; and
   (d) treating the patient having the abnormal phenotype with an inhibitor of aldose reductase.

* * * * *